(12) United States Patent
Walker et al.

(10) Patent No.: US 6,361,966 B1
(45) Date of Patent: Mar. 26, 2002

(54) OVER-EXPRESSION OF PROTEINS

(75) Inventors: John Ernest Walker, Cambridge (GB); Bruno Miroux, Paris (FR)

(73) Assignee: Medical Research Council (GB)

( * ) Notice: Subject to any disclaimer, the term of this patent is extended or adjusted under 35 U.S.C. 154(b) by 0 days.

(21) Appl. No.: 09/214,198

(22) PCT Filed: Jul. 11, 1997

(86) PCT No.: PCT/GB97/01879

§ 371 Date: Sep. 15, 1999

§ 102(e) Date: Sep. 15, 1999

(87) PCT Pub. No.: WO98/02559

PCT Pub. Date: Jan. 22, 1998

(30) Foreign Application Priority Data

Jul. 12, 1996 (GB) .............................................. 9614700

(51) Int. Cl.⁷ .......................... C12P 21/06; C12N 15/09; C12Q 1/02; C12Q 1/68; C07H 21/04

(52) U.S. Cl. ............................ 435/69.1; 435/6; 435/29; 435/69.7; 435/252.3; 435/471; 435/320.1; 536/23.1

(58) Field of Search ................................ 435/69.1, 440, 435/6, 29, 455, 468, 471, 325, 410, 523, 320.1, 69.7; 536/23.1

(56) References Cited

U.S. PATENT DOCUMENTS 5,429,948 A    7/1995   Crespi et al.

FOREIGN PATENT DOCUMENTS

| EP | 0 343 783 A | 11/1989 |
|----|-------------|---------|
| WO | WO 95 03413 A | 2/1995 |

*Primary Examiner*—David Guzo
*Assistant Examiner*—Gerald G. Leffers, Jr.
(74) *Attorney, Agent, or Firm*—Palmer & Dodge LLP

(57) ABSTRACT

The invention describes a method for selecting host cell mutants which are resistant to expression system toxicity, comprising the steps of growing an expression system comprising host cells transformed with an expression vector, inducing the expression system such that a toxic effect is observed, and selecting viable cells in which the expression vector continues to function. Cells thus obtained are useful for the expression of polypeptide gene products in microorganisms.

22 Claims, 5 Drawing Sheets

OVER-EXPRESSION OF PROTEINS

The present invention relates to novel host cells capable of over-expressing proteins at levels normally toxic thereto, and to methods of producing such bacteria and their use.

Microorganisms, and especially bacteria such as *Escherichia coli*, are among the most successful vehicles for over-expression of both prokaryotic and eukaryotic proteins (for reviews see Hockney, 1994: Grisshammer & Tate, 1995). However, expression systems employed to over-express such proteins are not always satisfactory. For example, over-expression of many prokaryotic proteins, including membrane proteins, some cytoplasmic proteins (Dong et al., 1995) and cell division proteins (de Boer et al., 1988; Gutzman et al., 1992) as well as the expression of toxic proteins such as DNAse (Doherty et al., 1993) is toxic to the host bacterium.

The expression of eukaryotic proteins in microorganisms can be equally problematical. Over expression of such proteins can also be toxic to the cell. Nonetheless, bacterial expression systems are used in industry and have been used to express a wide variety of proteins, including chymosin, insulin, interferons, insulin-like growth factors, antibodies including humanised antibodies, or fragments thereof. Given the widespread use of microorganisms for polypeptide expression in industry, there is a continuing need for improved expression systems.

Many different expression systems are known in the art for the expression of both endogenous and foreign proteins. In general DNA encoding the sequence of interest is contained in an expression vector, in some cases linked in-frame at the 5' or 3' end to another coding sequence so as to encode a fusion protein. The total coding sequence is operably linked to a promoter such that the promoter drives expression of the coding sequence. The coding sequence is also referred to herein as the "target gene".

The promoter is generally either a promoter native to the microorganism (for example the *E. coli* trpE promoter), a synthetic promoter such as the Tac promoter or a promoter obtainable from a heterologous organism, for example a virus, a bacterium or a bacteriophage such as phage λ or T7 which is capable of functioning in the microorganism. The promoter may be constitutive or, more preferably, inducible. The expression vector may also contain a selectable marker gene, which may be an antibiotic resistance gene such as an ampicillin, tetracycline, chloramphenicol or kanamycin resistance gene.

Many promoter systems are available, often from commercial sources, which are suitable for expression of polypeptides in *E. coli*. For example, the $P_{BAD}$ promoter from the araBAD (arabinose) operon has been used, and shows advantageous induction properties, being inducible 1200 fold over background (Guzman et al., 1995). Others include $P_{LAC}$, $P_{TAC}$, $P_{TRC}$, $P_L$ and $P_R$. These and other systems are known in the literature.

Of these, one widely used promoter is $P_{TAC}$ (De Boer et al., 1983). This promoter is a hybrid derived from the trp and lac promoters of *E. coli*, and is one of the most potent *E. coli* based promoter systems known. It is inducible by IPTG, as with the lac promoter.

In another very widely used expression system, the target gene is transcribed from the vector by T7 RNA polymerase (Studier et at., 1990). In the *E. coli* BL21(DE3) host strain, used in conjunction with pET vectors, the T7 RNA polymerase is produced from the λ-lysogen DE3 in the host bacterium, and its expression is under the control of the IPTG inducible lac UV5 promoter. This system has been employed successfully for over-production of many proteins, but in many cases significant over-production is hampered because of toxicity associated with the system (Studier et al., 1990: George et al., 1994). To date, it has widely been assumed that the toxicity was a function of the protein expressed in the expression system and that generally improved hosts would not be available (Studier et al., 1990).

The present invention surprisingly provides improved host cells which show a general improvement in tolerance of the toxic effects of expression systems.

SUMMARY OF THE INVENTION

In a first aspect, therefore, the invention provides a method for selecting host cell mutants which are resistant to expression system toxicity, comprising the steps of growing an expression system comprising host cells transformed with an expression vector, inducing the expression system such that a toxic effect is observed, and selecting viable cells in which the expression vector continues to function.

The invention also provides a host cell which is resistant to expression system toxicity.

Further aspects of the invention relate to more specific systems, for expressing particular classes of polypeptides, such as membrane proteins. Moreover, the invention provides host cells obtainable by the methods of the invention, especially bacterial host cells.

In a still further aspect of the invention, cells according to the invention may be employed in a method for the production of recombinant polypeptides which comprises transforming cells according to the invention with a vector encoding a nucleic acid sequence encoding the desired polypeptide and culturing the cells under conditions which allow for the expression of the polypeptide.

Surprisingly, the effect observed is general, in that it is observed whatever the target polypeptide which is encoded by the expression system. The cells are thus "resistant to expression system toxicity", as opposed to being resistant to the expression of a particular toxic gene.

The invention in particular relates to the expression of membrane proteins, such that they either accumulate in the cytoplasm as inclusion bodies or become incorporated into the membrane system of the host and are thus easily recoverable and/or available for screening in situ.

DETAILED DESCRIPTION OF THE INVENTION

Figure 1:
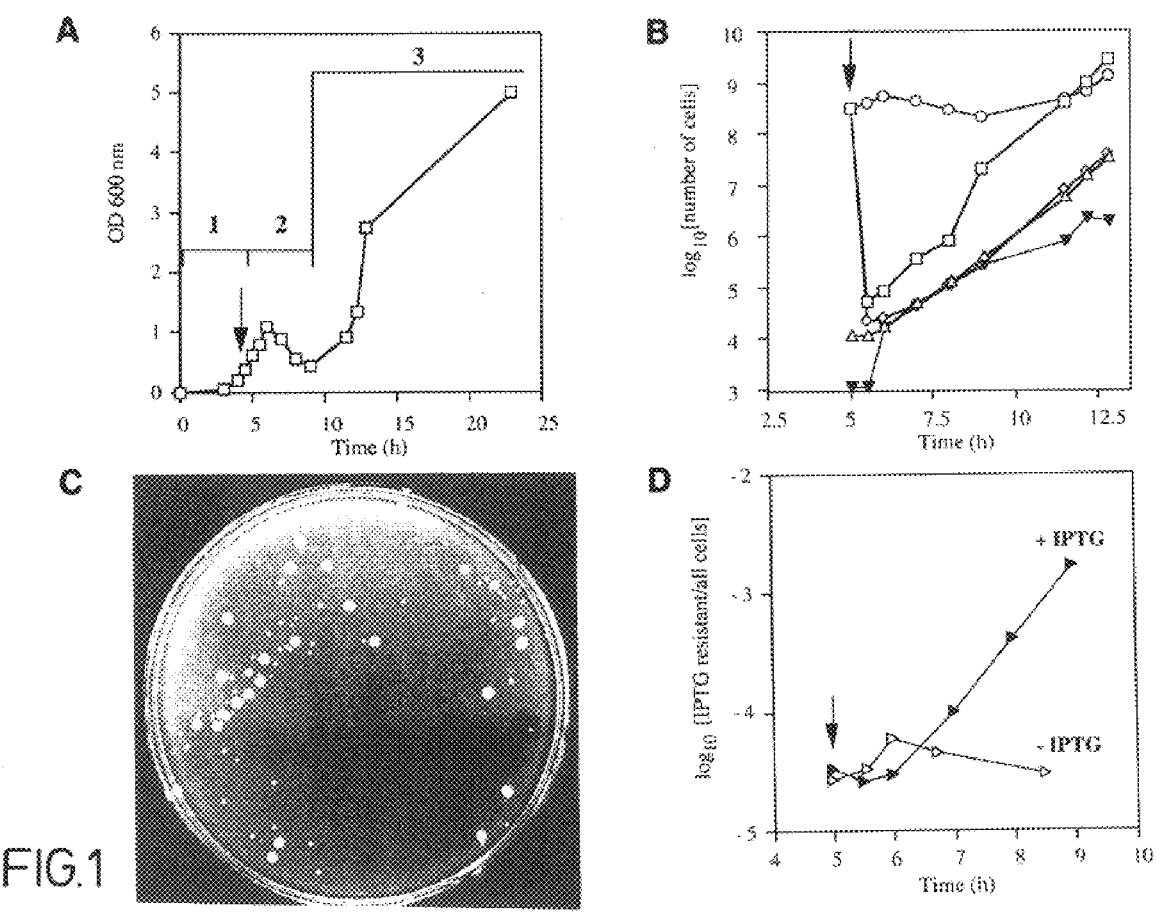
FIG. 1. Effect of expression of bovine OGCP on the growth of *E. coli* BL21(DE3) host cells. In parts (A), (B) and (D), the vertical arrow indicates the addition of the inducer IPTG to the liquid culture. Part (A): Three phases of growth are marked: 1, pre-induction; 2, post-induction cell death: 3, overgrowth of the culture. Parts (B)–(D): analysis of the bacterial population after induction of expression of the bovine OGCP. In (B), the analysis is performed on samples from part (A). The symbols used are as follows: ○, number of cells calculated from the optical density; □, number of viable cells on 2xTY plates; ◇, ampicillin resistant colonies; △, ampicillin and IPTG resistant colonies; ▼, small colonies resistant to both ampicillin and IPTG ("small" colonies were visible after 18 h incubation at 37° C., and their diameter was about 30%; smaller than that of normal "large" colonies). Part (C), large and small colony formation in the presence of ampicillin and IPTG. Part (D), the frequency of ampicillin and IPTG resistant colonies compared with the total population: ▷, non-induced culture; ▶, induced culture.

An "expression system" according to the present invention consists essentially of host cells transformed with one or more expression vectors encoding a polypeptide to be expressed. The toxicity associated with expression of foreign polypeptides in host cells is, surprisingly, only partly due to the protein being expressed. An important element in toxicity is the expression system itself: empty vectors can have toxic effects on induction. We have found that by recovering cells from a culture transformed with an expression vector following expression and induction of the target gene, and cultivating such cells under selective conditions, it is possible to recover from the culture cells which are inter alia resistant to expression system toxicity and capable of expressing high levels of target genes without the deleterious effects on the cells normally observed.

As noted above, the effect observed is general, in that it is observed whatever the target polypeptide which is encoded by the expression system. In certain instances, further improvements may be obtained which are related in a broad way to the expression of certain classes of polypeptide, for example membrane proteins. Preferably, however, the resistance of the host cell mutants is not specific to a target protein expressed in the expression system.

The nature of the mutations which take place in the host cells when treated by the method of the invention is not critical to the performance thereof, because the invention provides an essentially empirical process for the selection of mutants which selects mutants according to activity. However, it is likely that mutants according to the invention show a change in metabolic activity over non-mutant or wild-type cells. This decrease may be specific, in other words associated with a particular metabolic pathway, or general, in which case it may affect more than one pathway or system in the cell.

The expression system referred to herein consists essentially of a host cell transformed with an expression vector which encodes a target polypeptide gene product and, preferably, a selectable marker. Accordingly, the invention provides a method for improving an expression system comprising the steps of:

(a) preparing an expression system consisting essentially of a host cell transformed with an inducible expression vector encoding a target polypeptide and a selectable marker;

(b) culturing cells transformed with the expression system under selection pressure compatible with the selectable marker;

(c) inducing the expression system to produce the target polypeptide, such that a toxic effect is observable in the host;

(d) recovering host cells from the culture and growing them under a selection pressure and inducing conditions; and (e) selecting viable host cells which continue to produce the target polypeptide.

Vectors, expression vectors or otherwise, for use in the invention may be constructed according to protocols known in the art, as provided, for example, in Sambrook et al. (1989). cDNA or genomic DNA encoding a native or mutant target gene can be incorporated into vectors for manipulation. As used herein, vector (or plasmid) refers to discrete elements that are used to introduce heterologous DNA into cells for expression, manipulation or replication thereof. Selection and use of such vehicles are well within the skill of the person of ordinary skill in the art. Many vectors are available, and selection of appropriate vector will depend on the intended use of the vector, i.e. whether it is to be used for DNA amplification or for DNA expression, the size of the DNA to be inserted into the vector, and the host cell to be transformed with the vector. Each vector contains various components depending on its function (amplification of DNA or expression of DNA) and the host cell for which it is compatible. The vector components generally include, but are not limited to, one or more of the following: an origin of replication, one or more marker genes, an enhancer element, a promoter, a transcription termination sequence and a signal sequence.

Both expression and cloning vectors generally contain nucleic acid sequences that enable the vector to replicate in one or more selected host cells. Typically, in cloning vectors, this sequence is one that enables the vector to replicate independently of the host chromosomal DNA, and includes origins of replication or autonomously replicating sequences. Such sequences are well known for a variety of bacteria, yeast and viruses. The origin of replication from the plasmid pBR322 is suitable for most Gram-negative bacteria and the 2μ plasmid origin is suitable for yeast.

Most expression vectors are shuttle vectors, i.e. they are capable of replication in at least one class of organisms but can be transfected into another organism for expression. For example, a vector is cloned in *E. coli* and then the same vector is transfected into yeast cells even though it is not capable of replicating independently of the host cell chromosome. DNA may also be replicated by insertion into the host genome. However, the recovery of genomic DNA encoding target gene is more complex than that of exogenously replicated vector because restriction enzyme digestion is required to excise target gene DNA. DNA can be amplified by PCR and be directly transfected into the host cells without any replication component.

Advantageously, an expression and cloning vector may contain a selection gene also referred to as selectable marker. This gene encodes a protein necessary for the survival or growth of transformed host cells when grown in a selective culture medium. Host cells not transformed with the vector containing the selection gene will not survive in the culture medium under selective conditions. Typical selection genes encode proteins that confer resistance to antibiotics and other toxins, e.g. ampicillin, neomycin, methotrexate or tetracycline, complement auxotrophic deficiencies, or supply critical nutrients not available from particular growth media.

As to a selective gene marker appropriate for yeast, any marker gene can be used which facilitates the selection for transformants due to the phenotypic expression of the marker gene. Suitable markers for yeast are, for example, those conferring resistance to antibiotics G418, hygromycin or bleomycin, or provide for prototrophy in an auxotrophic yeast mutant, for example the URA3, LEU2, LYS2, TRP1, or HIS3 gene.

Since the replication of vectors is conveniently done in *E. coli*, an *E. coli* genetic marker and an *E. coli* origin of replication are advantageously included. These can be obtained from *E. coli* plasmids, such as pBR322, Bluescript© vector or a pUC plasmid, e.g. pUC18 or pUC19, which contain both *E. coli* replication origin and *E. coli* genetic marker conferring resistance to antibiotics, such as ampicillin.

Expression and cloning vectors usually contain a promoter that is recognised by the host organism and is operably linked to target gene nucleic acid. Such a promoter may be inducible or constitutive. The promoters are operably linked to DNA encoding target gene by removing the promoter from the source DNA by restriction enzyme digestion and inserting the isolated promoter sequence into the vector. Both the native target gene promoter sequence and many heterologous promoters may be used to direct amplification and/or expression of target gene DNA.

Promoters suitable for use with prokaryotic hosts include, for example, the β-lactamase and lactose promoter systems, alkaline phosphatase, the tryptophan (trp) promoter system and hybrid promoters such as the tac promoter. Their nucleotide sequences have been published, thereby enabling the skilled worker to operably ligate them to DNA encoding target gene, using linkers or adaptors to supply any required restriction sites. Promoters for use in bacterial systems will also generally contain a Shine-Delgarno sequence operably linked to the DNA encoding target gene. In the context of the present invention, the use of bacteriophage promoters, for example the T7 promoter, is particularly preferred.

Moreover, the target gene according to the invention may include a secretion sequence in order to facilitate secretion of the polypeptide from bacterial hosts, such that it will be produced as a soluble native peptide rather than in an inclusion body. The peptide may be recovered from the bacterial periplasmic space, or the culture medium, as appropriate.

Suitable promoting sequences for use with yeast hosts may be regulated or constitutive and are preferably derived from a highly expressed yeast gene, especially a *Saccharomyces cerevisiae* gene. Thus, the promoter of the TRP1 gene, the ADHI or ADHII gene, the acid phosphatase (PH05) gene, a promoter of the yeast mating pheromone genes coding for the α- or a-factor or a promoter derived from a gene encoding a glycolytic enzyme such as the promoter of the enolase, glyceraldehyde-3-phosphate dehydrogenase (GAP), 3-phospho glycerate kinase (PGK), hexokinase, pyruvate decarboxylase, phosphofructokinase, glucose-6-phosphate isomerase, 3-phosphoglycerate mutase, pyruvate kinase, triose phosphate isomerase, phosphoglucose isomerase or glucokinase genes, or a promoter from the TATA binding protein (TBP) gene can be used. Furthermore, it is possible to use hybrid promoters comprising upstream activation sequences (UAS) of one yeast gene and downstream promoter elements including a functional TATA box of another yeast gene, for example a hybrid promoter including the UAS(s) of the yeast PH05 gene and downstream promoter elements including a functional TATA box of the yeast GAP gene (PH05-GAP hybrid promoter). A suitable constitutive PH05 promoter is e.g. a shortened acid phosphatase PH05 promoter devoid of the upstream regulatory elements (UAS) such as the PH05 (−173) promoter element starting at nucleotide −173 and ending at nucleotide −9 of the PH05 gene.

An expression vector includes any vector capable of expressing target gene nucleic acids that are operatively linked with regulatory sequences, such as promoter regions, that are capable of expression of such DNAs. Thus, an expression vector refers to a recombinant DNA or RNA construct, such as a plasmid, a phage, recombinant virus or other vector, that upon introduction into an appropriate host cell, results in expression of the cloned DNA. Especially preferred are episomal plasmid vectors for use in *E. coli* hosts, such as the pET and pMW 7 vectors which employ the T7 polymerase expression system.

Construction of vectors according to the invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing target gene expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridisation, using an appropriately labelled probe based on a sequence provided herein, by analysis by polymerase chain reaction-based methods or by sequencing. Those skilled in the art will readily envisage how these methods may be modified, if desired.

The invention may be practised employing any microbial host. Particularly preferred are bacterial and yeast hosts. Although the present invention is described with particular relevance to *E. coli* other bacteria may also be used, in particular other members of the family Enterobacteriacae such as other members of the genera Escherichia or those of the genera Salmonella. Other bacteria include spore forming bacteria such as those of the genera Bacillus, e.g. *B. subtilis,* Thermophilus and Lactobacillus. Heterologous DNA may be introduced into host cells by any method known in the art, such as transfection with a vector encoding a heterologous DNA by the calcium phosphate coprecipitation technique or by electroporation. Numerous methods of transfection are known to the skilled worker in the field. Successful transfection is generally recognised when any indication of the operation of this vector occurs in the host cell. Transformation is achieved using standard techniques appropriate to the particular host cells used.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g. Sambrook et al., (1989) Molecular Cloning: A Laboratory Manual, Second Edition, Cold Spring Harbor Laboratory Press).

Transfected or transformed cells are cultured using media and culturing methods known in the art, preferably under conditions, whereby the target polypeptide encoded by the transferred nucleic acid is produced. The composition of suitable media is known to those in the art, so that they can be readily prepared. Suitable culturing media are also commercially available.

Cultivation of the host cells may take place in the presence of selection pressure, usually in the presence of an antibiotic which is metabolised by the selectable marker gene of the vector. The concentration of antibiotic used will depend upon the exact nature of the resistance gene and the concentration at which untransformed cells are killed by the antibiotic. In the case of ampicillin, somewhere between 20 and 200 $\mu$g per ml of culture will usually be sufficient, although this may be determined empirically if need be by those of skill in the art. In general, suitable concentrations of antibiotics may be determined by reference to standard laboratory reference books (e.g. Sambrook et al, 1989). A specific advantage of the present invention, however, is that cells may be cultivated for expression in the absence of antibiotic, due to the stability of the expression system. This can significantly decrease the costs of production and facilitate regulatory authority approval for a product.

Because of the toxicity to the cell of the expression system, the hosts initially will be cultivated under conditions where little or no expression of the target gene occurs so that log phase growth of the cells are achieved. For *E. coli* this will typically mean that the cells are grown to a density of around $10^6$ cells per ml, for example in the range of from $10^2$ to $10^7$ per ml. The cell density may be measured using optical density measurements. Alternatively, the cells may be grown for a suitable period of time, e.g. from 1 to 6, e.g. from 3 to 4 hours at 37° C.

The cells may also be cultured at a lower or higher temperature. This may be useful where for example the expression of the target polypeptide is linked to a temperature-sensitive gene. In such a situation the cells would first be grown at the non-permissive temperature, i.e. the temperature where expression of the target gene does not occur.

Following the culturing of the cells under selection pressure the culture will be induced to express the target gene. A number of inducible promoters operable in bacteria are available. Some promoters, such as the trpE promoter, are inducible by the presence or absence of metabolites or catabolites in the media (namely tryptophan in the case of the trpE promoter). Other promoters include the tac promoter or the lambda $P_R$ promoter.

A preferred promoter is however a bacteriophage promoter which requires a bacteriophage polymerase for expression. As mentioned above, a preferred promoter is the T7 promoter which may be used in conjunction with a cell in which the T7 polymerase gene has been cloned and placed under the control of a separate inducible promoter. The T7 polymerase is selective for its promoter binding site and is thus particularly useful since in the absence of T7 polymerase little expression of the target gene will occur. The gene encoding the polymerase is introduced into the cell in a lambda phage and is situated in the phage genome within the int gene so that the phage needs a helper phage for integration or excision from the genome. The polymerase gene is linked to the UV5 promoter which is inducible by isopropyl-$\beta$-D-thio-galactopyranoside (IPTG) so that addition of IPTG to the culture induces the production of T7 polymerase. Alternatively the gene may be introduced on a lambda phage by infection with an int phage such the CE6 phage which is commercially available (Novagen, Madison, USA).

Following induction of the target gene, toxic effects on the cell will be observed, and the culture should be maintained for a suitable period of time such that cell death starts to occur, and cells in the culture start to loose the vector encoding the target polypeptide. Usually the cells should be maintained in liquid culture until no more than 50% and preferably no more than 10%, e.g. 1% or 0.1% of cells retain the vector. This may be determined by plating duplicate aliquots of the culture on solid medium with and without the selection pressure and determining the ratio between the number of colonies which grow under selective and non-selective conditions.

Following growth and induction, the cells of the culture are recovered and grown on fresh medium under selection and inducing conditions. The fresh medium is desirably a solid medium, typically agar which contains the necessary nutrients for cell growth. Survivors are examined for the presence of the target gene. We have surprisingly found that some of the colonies recovered from this medium contain cells which are resistant to the toxic effects of the target gene. This is in contrast to normal practice in the art which has regarded the "spent" culture as a waste product following recovery of the target polypeptide. Resistant colonies according to the invention manifest themselves as small colonies, in contrast to large colonies, which have lost the ability to express the target gene.

The process may be repeated one or more times to improve resistance to toxicity.

As mentioned above, in a preferred aspect of the invention the bacteria used in the process of the invention express a bacteriophage RNA polymerase and wherein the vector comprises promoter sequences recognised by the polymerase. The polymerase is preferably T7 RNA polymerase, although other suitable polymerases include *E. coli* RNA polymerase.

A preferred strain of *E. coli* is a B strain, such as BL21 or a K strain such as JM109 or DK8. These strains are widely available in the art from academic and/or commercial sources. The B strains are deficient in the lon protease and other strains with this genotype may also be used.

Most preferably the strain is BL21(DE3), as disclosed in Studier et al, (1990). This is also available from Novagen. A preferred vector into which the target gene is inserted is pET, pRSET (Invitrogen) or pMW7 (Invitrogen) which both contain the T7 promoter. pET and pMW7 are also disclosed by Studier et al and Way et al., 1990 and are also generally available in the art. Other vectors include vectors containing the lambda $P_L$ promoter such as pLEX (Invitrogen. NL), vectors containing the trc promoters such as pTrcHisXpress™ (Invitrogen) or pTrc99 (Pharmacia Biotech, SE), or vectors containing the tac promoter such as pKK223-3 (Pharmacia Biotech) or pMAL (new England Biolabs, Mass, USA).

Target polypeptides which may be expressed in the bacteria and thus used to select bacteria with improved resistance to toxic expression systems include membrane proteins. The membrane proteins include foreign membrane proteins or endogenous membrane proteins. Examples of such proteins include the oxoglutarate-malate carrier protein (OCGP), phosphate carrier. ADP/ATP translocase, Bacillus PS3 alanine carrier, E. coli F-ATPase subunit b, E. coli F-ATPase subunit c, F-ATPase b-subunit. Examples of globular proteins include F-ATPase α-subunit. F-ATPase β-subunit, F-ATPase γ-subunit, F-ATPase δ-subunit, F-ATPase d-subunit. F-ATPase OSCP-subunit, F-ATPase $F_6$-subunit, F-ATPase inhibitor protein, *D. melanogaster* staufen protein and *Aequoria victoria* Green Fluorescent Protein (GFP). The various F-ATPase subunits may be from any suitable source, e.g. mammalian such as human or bovine, or bacterial.

These proteins have all been cloned and their sequences are readily available in the literature.

The terms "toxic" and "toxic effect" are relative terms which can be understood without difficulty in the art. For example, Studier et al (1990) refer to the problem of genes whose product is toxic to host cells without the necessity to define this term in further detail.

In general however toxicity may be manifested by a variety of effects on the cell, including impaired cell growth, decreased copy number, an increase in cells in the growth media lacking the plasmid (Studier et al., 1990), filamentation of bacterial cells (George et al, 1994), induction of the SOS response (Murli & Walker, 1993) and/or ribosomal disruption (Dong et al, 1995).

In the case of toxicity which is associated with the polypeptide produced by the expression system, the toxicity is often related to the level of expression which is achieved. In the case of endogenous polypeptides toxicity may occur when the polypeptide is expressed at levels which are non-physiological, for example at twice or more (five, ten or even up to a hundred times) the physiological level. In the case of heterologous polypeptides toxicity may occur at a variety of levels, depending upon the exact nature of the polypeptide.

In either case, toxic effects will generally be observed when the target protein is expressed in the *E. coli* cells at a level that would provide a convenient source of material for a variety of purposes such as structural studies or commercial recombinant production of proteins. Minimally this is likely to be about 1 mg of the target protein/liter of bacterial culture, and may be up to 5 mg/L, e.g. 10 mg/L, 100 mg/L, 500 mg/L or 1 g/L.

With strong promoters, such as the inducible T7 promoter system described herein, the expression of the target gene can occur such that target polypeptide produced by the gene amounts to at least 10%, in some cases at least 50% of all cellular protein in cells which retain the vector. In these cases the over-expression of the polypeptide will usually be toxic to a non-adapted cell.

In the case, however, where the toxic effects are due to factors other than the nature of the polypeptide, but are due to the expression system as such, the toxicity may not depend only on the level of expression of the target gene but also from the manner in which expression proceeds. It may depend from factors associated with the expression vector itself, such as plasmid copy number, promoter strength, the presence of cryptic promoters and the effects of antibiotic resistance genes. Moreover, it may depend from factors associated with the system as a whole, such as the coupling of transcription, translation and downstream processing and other biological factors. The interplay of these factors is not well understood.

In another preferred aspect of the invention, the vector further comprises a nucleic acid sequence encoding a polypeptide which serves as a detectable label and/or the target gene itself may encode a detectable label. This is useful in recovering colonies from the final step of the process of the invention as it provides a rapid confirmation that colonies observed have retained the vector and express the target protein. The detectable label gene may be the target gene, be placed in-frame with the target gene or may be a separate cistron in a di- or poly-cistronic operon with the target gene.

A suitable detectable label is Green Fluorescent Protein (GFP) although any other reporter protein using colour, fluorescence or antibody staining may be employed. Where a fluorescent label is used, the cells may be recovered from the culture and selected by fluorescence activated cell sorting (FACS). Alternatively, antibody detection of a membrane protein targeted to the surface of a cell can be used to select for cells overexpressing the membrane protein using a FACS approach.

Host cells, preferably bacterial host cells, obtainable by any of the method of the invention, optionally cured of the vector, also form a further aspect of the invention. Particular bacteria include *E. coli* C43(DE3) (ECCC B96070445), *E. coli* C41(DE3) (ECCC B96070444), *E. coli* DK8(DE3)S and *E. coli* C0214 (DE3). Such bacteria, when cured, provide a host for the expression of further proteins, especially proteins whose expression is toxic to bacteria.

It has been found that when expression systems which display toxicity are subjected to selection for vector maintenance, such as by antibiotic selection pressure, under conditions in which system toxicity is observable, mutants develop which retain the vector but lose the system toxicity phenotype. This phenomenon has not previously been observed; indeed Studier et al. (1990) ascribe all host survival under toxic conditions to vector loss or loss of expression.

Some vector loss is indeed observed, the hosts deriving an alternative antibiotic resistance means in order to survive. Other hosts, however, mutate to evolve a resistance to system toxicity. These hosts appear as small colonies on agar plates. These hosts are the hosts according to the invention and retain the ability to express the target gene from the expression vector.

In a further aspect the invention provides a method for the preparation of a recombinant polypeptide which method comprises:
   (a) transforming host cells according to the invention with a vector comprising a nucleic acid sequence encoding the polypeptide and appropriate control sequences;
   (b) culturing the transformed host cells under conditions which allow expression of the polypeptide; and
   (c) recovering the polypeptide.

Recombinant polypeptides producible in cells according to the invention by the above method include, but are not limited to, chymosin, insulin, an interferon, an insulin-like growth factor, an antibody including a humanised antibody, or a fragments thereof. Particularly preferred, however, are membrane proteins of prokaryotic and eukaryotic origin, including receptor proteins, chaperone proteins and fragments thereof, proteins of medical and pharmaceutical utility, nucleases and other enzymes useful as research tools, proteins involved in food processing, including brewing and vinification, in detoxification and in degradation of industrial and domestic waste.

It is observed that polypeptides expressed in host cells according to the invention are more likely to remain soluble than would otherwise be the case. In particular, polypeptides which are only partially soluble in unselected host strains, such as BL21(DE3), are more soluble or completely soluble when produced in cells according to the invention.

The temperature of the culture conditions is an important factor in determining polypeptide solubility. Preferably, therefore, the culture is carried out at a reduced temperature. Advantageously, cells are cultured at between about 30 and about 20° C., most preferably at about 25° C.

A particularly preferred category of recombinant polypeptides which may be produced by the method of the invention includes membrane proteins. Hitherto, such proteins have been difficult to produce in culture, especially bacterial cell culture, due to their toxicity. Moreover, in conventional expression systems, membrane proteins are not efficiently inserted into membranes on synthesis and are thus rarely functional.

The expression system of the invention, however, provides an efficient system for membrane protein expression. Particularly preferred are hosts derived from two or more rounds of selection, for example hosts such as C43(DE3) and C0214(DE3). Accordingly, the invention provides a host cell which has been subjected to two or more rounds of selection in accordance with the invention. Advantageously, hosts are specifically selected using the polypeptide which it is desired to produce as the target gene in the expression system.

Cells which have been exposed to two or more selection rounds are particularly advantageously employed in the expression of polypeptides targeted to the periplasm. For example, a polypeptide, which may be a membrane or globular polypeptide may be expressed as a fusion protein with a periplasmic localisation sequence. Preferably, a pET-based vector is used for such a purpose.

In a further embodiment, membrane polypeptides produced by hosts according to the invention are efficiently inserted into membrane systems. They can be recovered easily by disruption of host cells and separation of the membrane fraction by centrifugation.

Production of membrane proteins according to the invention may give rise to increased membrane production in the host. This phenomenon is observed to be a result of membrane protein production. particularly in C43(DE3), and is induced for example by expression of the b subunit of E. coli F-ATPase. In the event, however, that increase membrane production is not observed when expression of the desired recombinant membrane protein is induced, in a still further embodiment the invention provides a method for producing membrane proteins, comprising the steps of:

(a) transforming a host cell according to the invention with a first expression unit and a second expression unit, wherein the first expression unit expresses the b subunit of E. coli F-ATPase under the control of a first inducible promoter and the second expression unit expresses the desired membrane protein under the control of a second inducible promoter;

(b) inducing expression of E. coli F-ATPase b subunit from the first expression unit, and culturing the host cells such that membrane production is induced:

(c) inducing expression of the desired membrane protein from the second expression unit and culturing the host cells to produce the desired membrane protein; and (d) disrupting the host cells, separating the membrane and cytosolic fractions by centrifugation and recovering the desired membrane protein from the membrane fraction.

"Expression units" comprise a coding sequence under the control of a promoter which are capable of directing the expression of the encoded gene product. The may be present on separate vectors, or on the same vector. Where they are present on separate vectors, the vectors preferably have different expression characteristics.

By "different replication characteristics", it is intended to denote that the plasmids replicate independently of each other and thus avoid mutual exclusion during cell replication. This is best achieved by using two different origins of replication, although other mechanisms, for example involving the use of two different selection markers, may also be used.

The desired membrane protein may be any protein which is targeted to the membrane. This includes natural membrane proteins, which are naturally targeted to the membrane, as well as artificially targeted proteins produced by fusing a protein which is not normally targeted to the membrane with a membrane targeting sequence. Examples of membrane proteins include, but are not limited to, OGCP, MPCP, bovine ADP/ATP translocase, Bacillus PS3 alanine/$H^+$ carrier, E. coli F-ATPase subunits b and c, and bovine F-ATPase subunit bc.

Examples of membrane targeting sequences include, but are not limited to, the b or c subunits of E. coli F-ATPase.

Promoters suitable for expressing the polypeptides encoded by the first and second expression vectors include inducible promoters as set forth above, but especially the T7 promoter used in conjunction with a host cell carrying the T7 polymerase gene. Importantly, the promoters on the first and second expression vectors should be inducible by different inducers. Thus, if the first promoter is the T7 or Tac promoter, the second promoter should not be IPTG inducible.

For example, the $P_{BAD}$ promoter of the arabinose operon can be used, which is induced by the presence of arabinose in the growth medium. Alternatively, the Trp promoter may be used.

Origins of replication are known in the art and described above; a particularly useful origin in the present case, however, is the pACYC origin.

Induction of E. coli F-ATPase b subunit from the first expression vector leads to increased membrane formation in cells according to the invention. Preferably, the cells used are cells which have been subjected to two or more rounds of selection, advantageously with a membrane protein employed as a target gene in the selection procedure. This membrane protein may be any membrane protein, but is advantageously E. coli ATPase b subunit. Most preferably, the host cells are C43(DE3) cells.

After growth of the cells and induction of membrane formation, the desired membrane protein gene carried on the second expression vector may be induced. Preferably, before induction thereof, the induction of the first expression vector is terminated.

In an alternative embodiment, the invention provides a method for screening membrane proteins in host cells. When membrane proteins are inserted into the cell membrane, they are displayed at the surface thereof in a substantially correct orientation and may thus be screened with agents which bind to, affect or modulate these proteins. For example, receptor proteins may be displayed on host cell membranes and ligands screened by exposing the cells thereto under conditions which promote receptor-ligand co-operation.

Host cells according to the invention are particularly suitable for expression of membrane-targeted proteins in a screening assay. Preferably, the cells are cells which have been exposed to two or more rounds of selection, at least one round of which should be performed using a membrane protein gene as the target gene. Advantageously, the cells are C43(DE3) cells.

The orientation of display of proteins in the host cell membrane may be modulated in the case of protein fusions with membrane targeting subunits such as F-ATPase b or c subunits. As with Mal E and Lam B fusions (Tucker et al., 1996; Kiefer et al., 1996; Chapot, 1990), the b and c subunits of F-ATPase insert into the cell membrane in a different sense, on account of the c subunit having two transmembrane domains as opposed to the b subunit's single domain. This leads to insertion of the protein in opposite orientations, according to which subunit is selected.

In certain instances, it may be desired to express polypeptides which do not target to the membrane or which do not incorporate therein efficiently. In this case, the invention provides for the use of polypeptide fusions with a membrane-targeting protein, such as the b or c subunits of F-ATPase. Moreover, the invention may be used in conjunction with the enhanced membrane producing capabilities possessed by cells according to the invention. Accordingly, the invention provides a method of screening agents which bind to, affect or modulate a desired polypeptide, comprising the steps of:

(a) transforming a host cell according to the invention with a first expression unit and a second expression unit, wherein the first expression vector expresses the b subunit of *E. coli* F-ATPase under the control of a first inducible promoter and the second expression vector expresses the desired polypeptide under the control of a second inducible promoter;

(b) inducing expression of *E. coli* F-ATPase b subunit from the first expression unit, and culturing the host cells such that membrane production is induced:

(c) inducing expression of the desired membrane protein from the second expression unit and culturing the host cells to produce the desired membrane protein;

(d) immobilising cell membranes on a support and exposing the cells to the agent to be screened under conditions which promote the interaction of the agent with the polypeptide.

The desired polypeptide may be any polypeptide for which it is desired to identify an interaction with the agents to be screened. However, membrane proteins, in particular receptor proteins, are particularly indicated.

Membranes may be obtained from disrupted cells, from which they can be easily isolated, for example by centrifugation, or may be in the form of intact cells. Pat of the membrane fraction from a disrupted cell according to the invention is obtained in the form of liposome-like vescicles, which may be inmmobilised on liposome-specific supports such as that available from Biocore.

If necessary, the phospholipid levels in the membranes may be adjusted to mimic the levels present in the natural environment of the polypeptide to be screened.

Methods for surveying ligand binding to membrane proteins are well known in the art. The main techniques used for separation of the free ligand from the bound ligand include rapid filtration, centrifugation, dialysis, gel filtration, precipitation or absorption. Alternatively, the "liposomes" containing the polypeptide to be screened are bound to a support compatible with the Biocore system. A library of ligands is generated and ligands are screened for their ability to bind the fusion protein. Ligands having a high binding constant to the MalE-NTR fusion protein are analysed further in vitro.

Although the selection procedure presented here is empirical, it has the advantage that it encompasses the entire complexity of the biology of the expression system, and it has provided an efficient means of modifying it. The method takes advantage of a population of host cells selected under conditions of induction and marker selection, that previously had been described incorrectly as only containing cells that have lost the ability to express the target DNA (Studier et al., 1990). As we have shown, two sub-populations giving rise to large and small colonies are present, and the latter contains cells that over-express the target protein better than the original host. Therefore, the procedure allows the expression system to be adapted and optimised for the expression of a particular protein, and it may be beneficial in other instances (including both globular and membrane proteins) to use the selection protocol to select a wider range of host strains derived, for example, from BL21(DE3), C41(DE3) and C43(DE3). In this way it may be possible to tailor the expression system by selection and thereby, for example, to prevent the formation of inclusion bodies, and to overcome toxic effects of various severities and origins.

It should be noted that removal of the toxic effects of an expression plasmid will not automatically guarantee that the protein is produced in large amounts, and to achieve this objective it may be necessary, for example, additionally to prevent mRNA degradation, to remove undesirable features in the coding sequence that impede translation (Kane, 1995), or to prevent proteolytic degradation.

The invention is further described, for the purposes of illustration only, in the examples, with reference to the figures.

EXAMPLES

Abbreviations Used

OGCP, oxoglutarate-malate transport protein from mitochondria; F-ATPase, $H^+$-transporting $F_1F_O$-ATPase; OSCP, oligomycin sensitivity conferral protein, a subunit of bovine F-ATPase; GFP, green fluorescent protein from the jelly-fish, *Aequoria Victoria;* IPTG, isopropyl-2-D-thiogalactopyranoside: EDTA, ethylenediamine-tetraacetic acid; PCR, polymerase chain reaction; SDS-PAGE, sodium dodecyl sulphate-polyacrylamide gel electrophoresis; expression plasmid names consist of the name of the plasmid vector, followed in parenthesis by the recombinant protein they encode.

Example 1

Toxic Effects of Polypeptide Expression in *E. coli* Expression System Toxicity

The toxic effects of the over-expression of seven membrane proteins (see Table 1) cloned in pET and related expression plasmids towards the *E. coli* BL21(DE3) host cells are investigated by attempting to grow cells containing the plasmids on two sets of agar plates, one containing IPTG and the other lacking the inducer. The proteins investigated are bovine OGCP, bovine phosphate carrier and bovine ADP/ATP carrier, all three being members of a super-family of transport proteins with six transmembrane spans (Walker & Runswick, 1993), subunits b and c of the *E. coli* F-ATPase with one and two transmembrane spans, respectively (Fillingame, 1990), and a fusion protein between bacteriophage T7 10a protein and the alanine-H$^+$ carrier from Bacillus PS3, which is thought to have 10–12 transmembrane α-helices (Kamata et al., 1992). In earlier studies, OGCP had been shown to be over-produced at high levels (10 mg per liter of bacterial culture) in *E. coli* BL21(DE3) (Fiermonte et al., 1993).

None of the seven vectors produce colonies on the plates containing IPTG, and in the absence of IPTG only very small colonies are formed from cells containing plasmids for the b-subunit of *E. coli* F-ATPase, for the bovine ADP/ATP carrier, and for the alanine-H$^+$ carrier. The cells in these very small colonies are not viable, and therefore it would not be possible to produce inocula for over-expression cultures in liquid media. Small viable colonies are obtained with the plasmid for *E. coli* subunit c. Similar experiments are conducted with vectors for ten globular proteins (see Table 1); none of them form colonies in the presence of IPTG.

Therefore, all seventeen of the expression plasmids that are examined produce toxic effects on the BL21(DE3) host, with a wide spectrum of severity. The plasmids encoding membrane proteins are the most toxic, but among plasmids encoding membrane proteins, the one encoding the OGCP is the least toxic.

Expression Vector Toxicity

A control experiment is conducted with five different expression vectors from the pET family, all of them lacking a target gene for possible over-expression. They are pMW7, pET17b (containing an N-terminal T7 tag), pET23a (containing a N-terminal T7 tag and a C-terminal His-tag), pET29a (containing an S-tag) and pGEMEX-1 (containing a gene 10a fragment). Surprisingly, none of the cells containing the "empty" plasmids produced colonies in the presence of IPTG, except for pET 17b, which gave very small colonies, demonstrating that the plasmids themselves are intrinsically toxic to *E. coli* BL21(DE3) host cells.

Growth and Gene Expression in Liquid Culture

The inhibitory effects of the pMW7 (OGCP) expression vector on *E. coli* BL21(DE3) are also studied in liquid culture containing ampicillin. The culture is grown for 4 hours before addition of the inducer, IPTG [see phase 1 in FIG. 1(A)]. One hour later, the cells have stopped dividing and the optical density of the culture has decreased (phase 2). After a further 5–6 hours, the optical density rises again (phase 3) and eventually reaches a value greater than 5.

Results are shown in FIG. 1. In parts (A), (B) and (D), the vertical arrow indicates the addition of the inducer IPTG (final concentration 0.7 mM) to the liquid culture. Part (A), a fresh colony of the host containing the plasmid pMW7 (OGCP) is inoculated into 2xTY medium (50 ml) supplemented with ampicillin (final concentration 50 μg/ml). Three phases of growth are marked: 1, pre-induction; 2, post-induction cell death; 3, overgrowth of the culture. Parts (B)–(D) show an analysis of the bacterial population after induction of expression of the bovine OGCP. Portions (100 μl) of each dilution (1 in 10, 1 in 10$^2$, 1 in 10$^3$, 1 in 10$^4$ and 1 in 10$^5$) are spread on three sets of agar plates, IPTG (0.7 mM, final concentration) and ampicillin (50 μg/ml), ampicillin alone, and no additives, respectively. The number of viable cells is determined by counting the colonies on the most suitable plate (100–300 colonies per plate). In (B), the analysis is performed on samples from part (A). The symbols used are as follows: ○, number of cells calculated from the optical density; □, number of viable cells on 2xTY plates; ◇, ampicillin resistant colonies; △, ampicillin and IPTG resistant colonies; ▼, small colonies resistant to both ampicillin and IPTG ("small" colonies are visible after 18 h incubation at 37° C., and their diameter is about 30%; smaller than that of normal "large" colonies). Part (C) shows large and small colony formation in the presence of ampicillin and IPTG of a sample of cells from a liquid culture taken 11.5 hours after induction by IPTG. In part (D), the frequency of ampicillin and IPTG resistant colonies is compared with the total population: ▷, non-induced culture; ▶, induced culture.

The maximal level of expression of the OGCP is attained 3 hours after addition of inducer, and it diminished thereafter. Therefore, phase 3 corresponds to the outgrowth of cells that have lost the ability to express the target gene. Similar three-phase growth curves have been observed in our studies of all of the proteins that have been over-produced in *E. coli* BL21(DE3). Some variation is observed in the length of the lag in phase 1 from 3 hours (GFP) to 10 hours (*E. coli* F-ATPase subunit c), and in maximal cell density in phase 2 from 0.5–2.0, depending on the degree of toxicity associated with the plasmid.

The toxicity mediated by IPTG induction of OGCP expression in *E. coli* BL21(DE3) in a liquid culture is investigated by plating the cells in the absence of selection pressure, in the presence of ampicillin, and in presence of both ampicillin and IPTG. After 30 minutes, the number of viable cells decreases dramatically from 10$^8$ to 10$^4$ even in the absence of ampicillin (see FIG. 1B). The optical density of the culture is still increasing at this juncture, and so the cells are dying but have not lysed. In the residual viable population, only 10% of the bacteria retain ampicillin resistance 2 hours after induction. and 3 hours later only 1% of the population is resistant to the antibiotic. Eight hours after induction, the number of viable cells equals the number of cells calculated from the optical density, showing that the culture now contains only cells that have lost the plasmid.

The ampicillin resistant cells are also resistant to IPTG (FIG. 1B), and the colonies contain two sub-populations of larger and smaller sizes (FIG. 1C). Neither of these phenomena have been described in previous investigations of this expression system (Studier et al., 1990). In a separate control experiment where no IPTG is added to the liquid culture, the plasmid is stable, and the number of viable cells is similar to the number of cells calculated from the optical density. However, on plates, a small fraction of the population is again resistant to IPTG. In the uninduced liquid culture, the ratio of cells resistant to IPTG compared to the total number of cells is stable at around 3×10$^{-5}$, whereas induction of expression by addition of IPTG increased this ratio to 3×10$^{-3}$ (FIG. 1D). Therefore, the expression of the OGCP in *E. coli* BL21(DE3) grown in liquid cultures has apparently increased the number of colonies resistant to IPTG.

Example 2

Selection of Mutant Host Strains (A) Isolation of C41(DE3)

Figure 2:
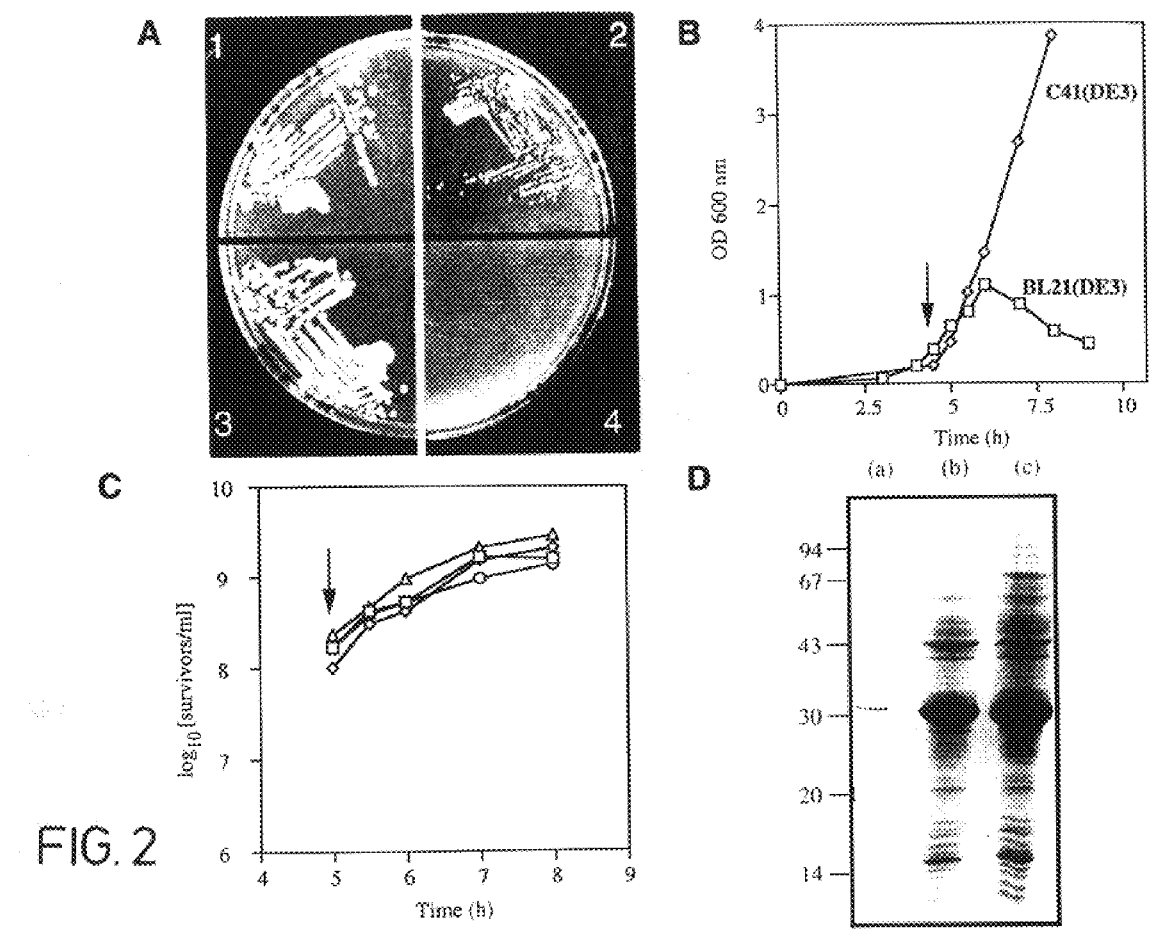
FIG. 2. Comparison of the expression of the OGCP in *E. coli* BL21(DE3) and C41(DE3) hosts. Part (A), comparison of phenotypes of *E. coli* BL21(DE3) and mutant C41(DE3), both containing pMW7(OGCP). Quadrants 1 and 2, *E. coli* C41(DE3), in the absence and presence of IPTG, respectively; quadrants 3 and 4, *E. coli* BL21(DE3) in the absence and presence of IPTG, respectively. Part (B), growth of the two strains containing pMW7(OGCP). Part (C), analysis of the bacterial population in the liquid culture. The arrows in (B) and (C) indicate the addition of inducer. ○, number of cells calculated from the optical density; □, number of cells able to grow on 2xTY plates; ◇, ampicillin resistant colonies; △, colonies resistant to both ampicillin and IPTG. Part (D), expression of the OGCP analysed by SDS-PAGE.

The apparent increase in the frequency of mutants by over-expression of the OGCP on *E. coli* BL21(DE3) presents the opportunity to select mutant host strains that might be more tolerant to over-expression of OGCP. The first round of selection is conducted with *E. coli* BL21(DE3) transformed with pMW7(OGCP). Four hours after induction, a 100-fold dilution of cells from the culture is plated on solid medium containing IPTG, giving subpopulations of large and small colonies as before (FIG. 1C). Three large colonies and one small colony are examined for their ability to express the OGCP in liquid media. No OGCP is produced by cells grown from the large colonies, but a culture grown from the small colony is found to produce OGCP and to continue growing in the presence of IPTG, eventually attaining a saturation optical density similar to control cultures grown in the absence of inducer. The strain of cells from the small colony is named $E.$ $coli$ C41(DE3). This is shown in FIG. 2, in which part (A) shows a comparison of phenotypes of $E.$ $coli$ BL21(DE3) and mutant C41(DE3), both containing pMW7(OGCP). Quadrants 1 and 2 contain $E.$ $coli$ C41(DE3), in the absence and presence of IPTG, respectively; quadrants 3 and 4 contain $E.$ $coli$ BL21(DE3) in the absence and presence of IPTG, respectively. The phenotype of C41(DE3) is stable; it continues to give rise to small colonies in the presence of IPTG, and to grow and to produce the OGCP in liquid cultures in the presence of inducer.

A comparison of the expression characteristics of C41(DE3) and BL21(DE3) appears in FIG. 2 (B–D), in which part (B) shows growth of the two strains containing pMW7(OGCP). Part (C) shows an analysis of the bacterial population in the liquid culture. The arrows in (B) and (C) indicate the addition of inducer. ○, number of cells calculated from the optical density; □, number of cells able to grow on 2xTY plates; ◇, ampicillin resistant colonies; Δ, colonies resistant to both ampicillin and IPTG. Part (D) shows the expression of the OGCP analysed by SDS-PAGE. The cultures are grown in 250 ml of broth. At the end of the expression experiment, generally 3 h for BL21(DE3), 18 h for C41(DE3), cells are centrifuged (7,000×g, 10 minutes) and re-suspended in buffer (20 ml) consisting of 10 mM Tris.HCl (pH 8.0), 1 mM EDTA and 0.001% (w/v) phenyl-methylsulphonyl fluoride. Bacteria containing overproduced proteins are passed twice through a French pressure cell (pre-cooled to 4° C.), inclusion bodies are collected by centrifugation (10 minutes, 10,000×g), and the membrane and cytosolic fractions are separated by ultra-centrifugation (2 h, 100,000×g).

In both cases, the protein forms inclusion bodies in bacterial cytoplasm. They are each re-suspended in 4 ml of buffer and 1 μl is analysed on the gel, which is stained with PAGE 83 dye. At the left hand side, the positions of molecular weight markers are indicated. Lane (a), OGCP expressed in $E.$ $coli$ BL21(DE3) 3 h after induction; lane (b), OGCP expressed in C41(DE3) 3 hours after induction in medium lacking ampicillin; lane (c), OGCP expressed in C41(DE3) 18 hours after induction by IPTG added at the starting point of the culture. In this experiment, no ampicillin is used in the medium, demonstrating the stability of the host.

The Mutation is in the Host

Plasmid pMW7(OGCP) is re-isolated from cells of $E.$ $coli$ C41(DE3), and is transformed back into $E.$ $coli$ BL21(DE3), restoring the toxic phenotype. Strain $E.$ $coli$ C41(DE3) is cured of pMW7(OGCP) by growth in liquid medium in the absence of ampicillin. Each day, a portion of the culture is diluted 1000-fold, and plated out in the presence of IPTG and in the absence of ampicillin. After 7 days, a large colony lacking the plasmid arose. Re-transformation of cells from this colony with pMW7(OGCP) restored the ability to grow in the presence of IPTG in liquid culture and to over-express the OGCP. Therefore, the mutation affecting over-expression of the OGCP is in strain C41(DE3), and not in the plasmid pMW7(OGCP).

(B) Isolation of C43(DE3)

Subsequently, it has proved to be possible to over-express many other proteins without toxic effects in $E.$ $coli$ C41(DE3) (see below). However, the toxicity of over-expression of certain proteins, including the b subunit of $E.$ $coli$ F-ATPase, persisted in strain C41(DE3). Therefore, a second round of selection is conducted on $E.$ $coli$ C41(DE3) transformed with pMW7(Ecb). From fifteen small colonies arising by plating in the presence of IPTG, one is found that over-expresses subunit b and continues to grow after induction. This strain is named $E.$ $coli$ C43(DE3), and the additional mutation is again shown to be associated with the bacterial genome. Similar to strain C41(DE3), the phenotype of C43(DE3) is stable (see FIG. 3A, which shows a comparison of phenotypes of $E.$ $coli$ C41(DE3) and mutant C43(DE3), both containing pMW7(Ecb). Quadrants 1 and 2, $E.$ $coli$ C43(DE3), in the absence and presence of IPTG, respectively; quadrants 3 and 4, $E.$ $coli$ C41(DE3) in the absence and presence of IPTG, respectively). Moreover, In contrast to their toxic effects on $E.$ $coli$ BL21(DE3), "empty" plasmids do not inhibit the growth of either the C41(DE3) or C43(DE3) strains.

It should be emphasised that the number of small colonies and the proportion of those small colonies that are competent for expression of a target protein, differ widely according to the toxicity of the expression plasmid. With relatively non-toxic plasmids such as pMW7(OGCP) and pMW7(GFP), encoding the green fluorescent protein, small colonies competent for over-expression are common and easily identifiable, whereas with more toxic plasmids such as pMW7(Ecb), mutants of C41 (DE3) expressing subunit b are rare.

(C) Isolation of C0214

Another polypeptide which is found to display residual toxicity in C41(DE3) is bovine mitochondrial phosphate carrier protein (MPCP), which is related to OGCP (see Runswick et al., 1987). Selection for mutants of C41(DE3) expressing MPCP, using a method exactly analogous to the methods employed for the original selection of C41(DE3) and the subsequent selection of C43(DE3), gives rise to C0214(DE3), which is resistant to the effects of MPCP expression.

It is postulated that this mutant, in addition to the general mutation present in C41(DE3), possesses a specific mutation which favours MPCP expression by tackling MPCP toxicity in a more direct manner.

(D) Isolation of DK8(DE3)S

Cells of $E.$ $coli$ strain DK8 (ATPase) are lysogenised with phage λ DE3 using a lysogenisation kit from Novagen according to the instruction supplied therein. This transfers the T7 RNA polymerase gene, under control of an IPTG-inducible Lac promoter. Lysogenised bacteria are plated out as described above and the smallest colonies picked. These colonies have the lowest levels of T7 polymerase expression.

This strain, DK8(DE3)S is tested as described in Example 1 for BL21(DE3). The growth characteristics are found to be identical—the induction of an expression vector, whether comprising a target gene or not, is toxic to the host. When expressing GFP, no colonies can be seen on IPTG induction, implying that the system is toxic. In the absence of IPTG, fluorescent colonies are obtained, which indicates the system to be leaky.

The selection procedure as described for BL21(DE3) is applied to DK8(DE3)S. The resultant colonies are of two types: small colonies which fluoresce on IPTG induction and large colonies which do not fluoresce. This is entirely consistent with the results obtained for BL21(DE3), in which the large colonies have lost the ability to express the target gene. One small colony was picked and cultured to produce the new mutant strain DK8(DE3)S.

Isolation of BL21S

Cells of strain BL21, lacking a DE3 lysogen, are mutated as described above for BL21(DE3) cells in order to obtain the mutant BL21S.

The target gene employed for the selection procedure, a GST-ADP1 fusion, shows toxicity in the BL21 host under inducing conditions when under control of the hybrid Tac promoter. Accordingly, BL21 cells are transfected with a Tac/target gene construct and cultures as set out for BL21 (DE3) cells.

When plated out, both small and large colonies are obtained. The large colonies no longer express the target gene. The small colonies retain the ability to express the target gene on induction of the Tac promoter, and are referred to as BL21S. Expression of the target gene in BL21S cells is higher than in BL21 cells.

Example 3

Expression of Polypeptides in Mutant Hosts

Figure 3:
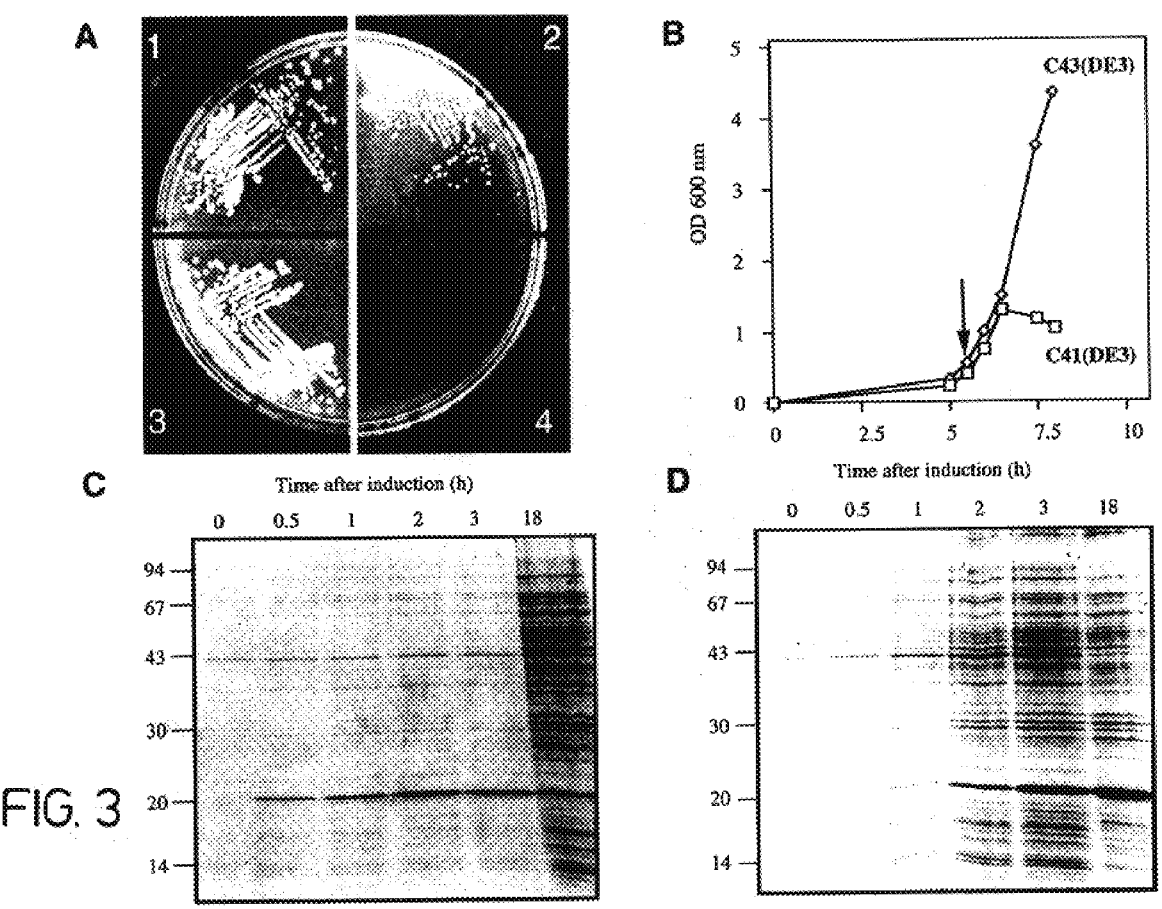
FIG. 3. Comparison of the expression of subunit b of *E. coli* F-ATPase in *E. coli* C41(DE3) and C43(DE3) hosts. Part (A), comparison of phenotypes of *E. coli* C41(DE3) and mutant C43(DE3), both containing pMW7(Ecb). Quadrants 1 and 2. *E. coli* C43(DE3), in the absence and presence of IPTG, respectively; quadrants 3 and 4, *E. coli* C41(DE3) in the absence and presence of IPTG, respectively. Part (B), growth curves of *E. coli* C41(DE3) and C43(DE3) expressing subunit b. The arrow indicates the induction of expression by IPTG. Parts (C) and (D), SDS-PAGE analysis of the expression of the b-subunit in *E. coli* C41(DE3) and C43 (DE3), respectively.

The advantages of strains C41(DE3) and C43(DE3) as hosts for over-expression of the OGCP and subunit b of the F-ATPase, respectively, are illustrated in FIGS. 2 and 3. FIG. 2 is discussed in the preceding Example; FIG. 3 shows comparison of the expression of subunit b of *E. coli* F-ATPase in *E. coli* C41(DE3) and C43(DE3) hosts. Freshly transformed colonies of C41(DE3) and C43(DE3) each containing pMW7(Ecb) are inoculated into 2xTY medium (50 ml) and grown at 37° C. Part (A), Part (B), growth curves of *E. coli* C41(DE3) and C43(DE3) expressing subunit b. The arrow indicates the induction of expression by IPTG. Parts (C) and (D), SDS-PAGE analysis of the expression of the b-subunit in *E. coli* C41(DE3) and C43 (DE3), respectively. The equivalent of 5 μl of culture is analysed at the times indicated above each slot. On the left hand side, the migration positions of standard proteins are indicated. The gel is stained with Coomassie 83 dye.

Both parental strains stop growing after induction of expression, whereas the mutant hosts continue to grow to high cell densities (see FIGS. 2B and 3B). By analysis of the cell population in the culture after induction of over-expression (FIG. 2C), it is apparent that pMW7(OGCP) remains stable in strain C41 (DE3), and in addition, the number of viable cells correlates with the number of cells calculated from the optical density. In C41(DE3), at least 10 times more OGCP is expressed than in BL21(DE3) [FIG. 2D, lanes (a) and (b)]. Moreover, strain C41(DE3) containing pMW7(OGCP) can be grown in 2xTY broth, containing IPTG but lacking ampicillin, without overgrowth [FIG. 2D, lane (c)]. The final cell density in C41(DE3) is six times greater than in BL21(DE3), and therefore the amount of OGCP produced per cell is somewhat higher in C41(DE3) than in BL21(ED3).

The course of expression of the *E. coli* F-ATPase b subunit in C41(DE3) and C43(DE3) differs (see FIGS. 3C and 3D), the onset of protein production being delayed in C43(DE3) by about one hour relative to C41(DE3). Three hours after induction, three times more protein has been produced in C43(DE3) than in C41(DE3); 15 hours later the amount of subunit b in C41(DE3) has decreased because the culture has become overgrown by cells that have lost expression capacity, as discussed above. Less subunit b is produced per cell in C43(DE3) than in C41(DE3), but the global amount of protein produced per liter of culture is higher in C43(DE3) because the cells continue to divide after induction of expression.

Figure 4:
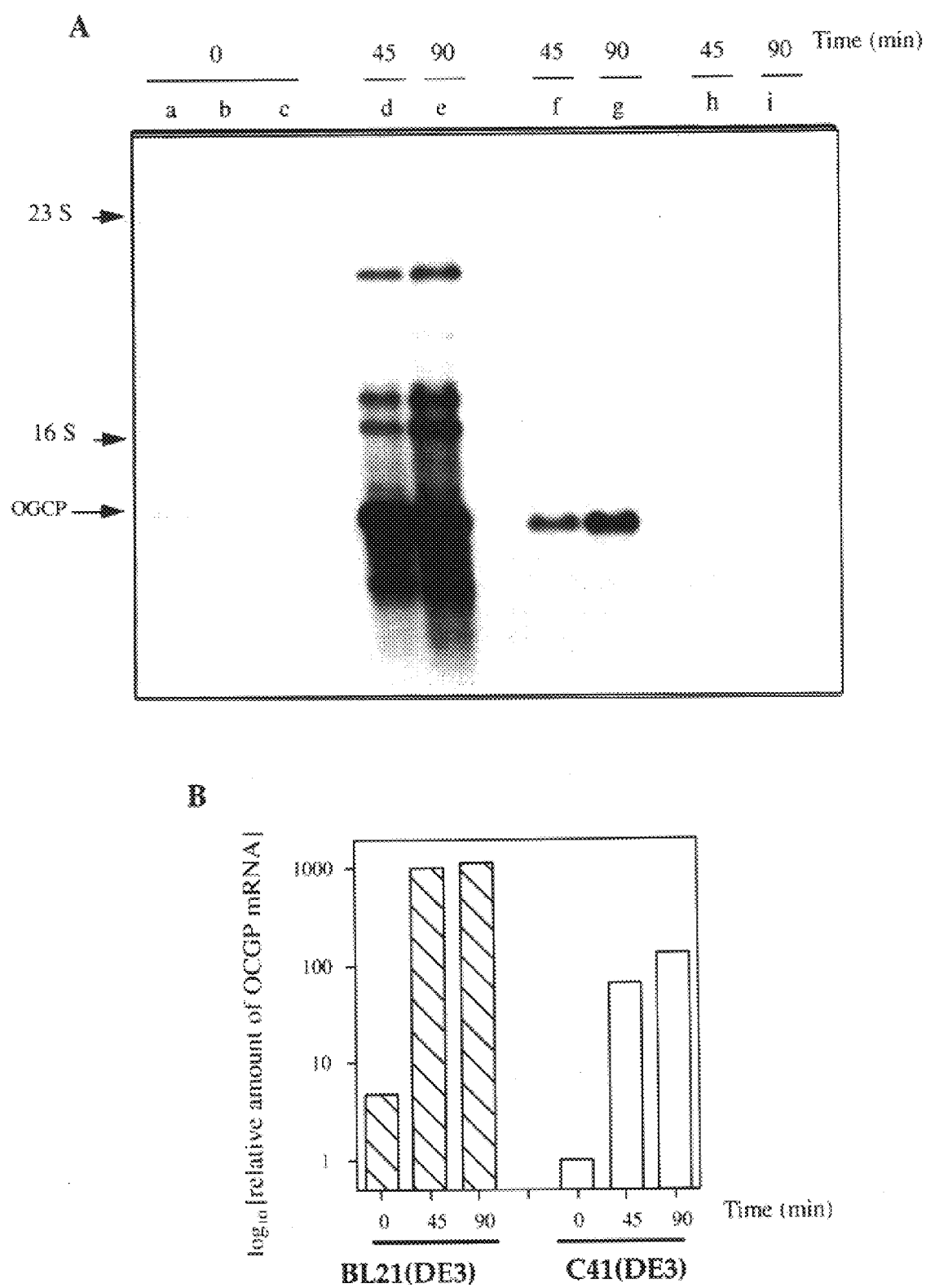
FIG. 4. Analysis of transcripts of the OGCP in *E. coli* BL21(DE3) and C41(DE3). Part (A), Autoradiograph of the membrane after 15 minutes exposure. Lanes (a), (d) and (e), RNA samples of BL21(DE3) expressing the OGCP; lanes (b), (f), and (g), RNA samples of C41(DE3) expressing the OGCP; lanes (c), (h) and (i), control RNA samples from C41(DE3) expressing the *E. coli* F-ATPase b-subunit. Samples are taken at various times after induction, as shown on top. The migration positions of the OGCP mRNA, and of the 16S and 23S ribosomal RNAs are indicated on the left. Part (B), relative amounts of the OGCP mRNA, estimated by densitometry of the appropriate bands on two different exposures of the membrane. In C41(DE3), the signal at time zero is chosen as reference.

Transcription of the gene for the OGCP is compared in BL21(DE3) and C41(DE3) hosts (see FIG. 4). RNA samples from cells of *E. coli* BL21(DE3) and C41(DE3) (4 ml), both containing the expression plasmids for the OGCP and subunit b of *E. coli* F-ATPase, are prepared according to Ausubel et al. (1987) and Uzan et al. (1988), respectively. RNA (3 μg) is fractionated by electrophoresis under denaturing conditions in a 1% agarose gel, and then transferred to a Hybond-N membrane. Pre-hybridisation and hybridisation of the membrane are carried out for 18 h at 42° C. The DNA probe for the bovine OGCP, corresponding to its complete coding sequence, is amplified from a plasmid by PCR, and radio-labelled with [α-$^{32}$P]-dCTP (50 μCi) by use of an oligonucleotide labelling kit (Pharmacia Biotech Ltd, St. Albans, Herts AL1 3AW, U.K.). The membrane is hybridised in the presence of the probe, washed twice at 42° C. in 2xSSC buffer containing 0.1% SDS, and twice at 65° C. in 0.1xSSC buffer containing 0.1% SDS [SSC buffer consists of 3 M sodium chloride and 0.3 M sodium citrate, pH 6.5]. The radioactivity on the membrane is measured by densitometry with a computing densitometer (Molecular Dynamics, model 300A with ImageQuant version 3.2 software) of a radioautograph exposed to Fuji RX film. Part (A) shows an autoradiograph of the membrane after 15 minutes exposure. Lanes (a), (d) and (e), RNA samples of BL21(DE3) expressing the OGCP; lanes (b), (f), and (g), RNA samples of C41(DE3) expressing the OGCP; lanes (c), (h) and (i), control RNA samples from C41(DE3) expressing the *E. coli* F-ATPase b-subunit. Samples are taken at various times after induction, as shown on top. The migration positions of the OGCP mRNA, and of the 16S and 23S ribosomal RNAs are indicated on the left. Part (B) shows the relative amounts of the OGCP mRNA, estimated by densitometry of the appropriate bands on two different exposures of the membrane. In C41(DE3), the signal at time zero is chosen as reference. The main RNA band has migrated further than 16S ribosomal RNA to a position corresponding to an mRNA of about 1 kilobase, as expected for the OGCP. Three larger RNAs, also detected with the OGCP probe, arise by the T7 RNA polymerase transcribing beyond the T7 transcriptional terminator, which is immediately after the OGCP gene in the plasmid. In longer exposures of the blot, similar bands can be seen in C41(DE3) also, but in relatively lower amounts compared with the main band in BL21(DE3). The basal level of OGCP mRNA synthesis in BL21(DE3) is five times higher than in C41(DE3) (see FIG. 4B), and the maximal amount of OGCP mRNA synthesised after induction is about ten times greater in BL21(DE3) than in C41(DE3). Moreover, the maximum amount of OGCP mRNA appears to have been reached after 45 minutes in BL21(DE3) and at least 45 minutes later in C41(DE3).

Figure 5:
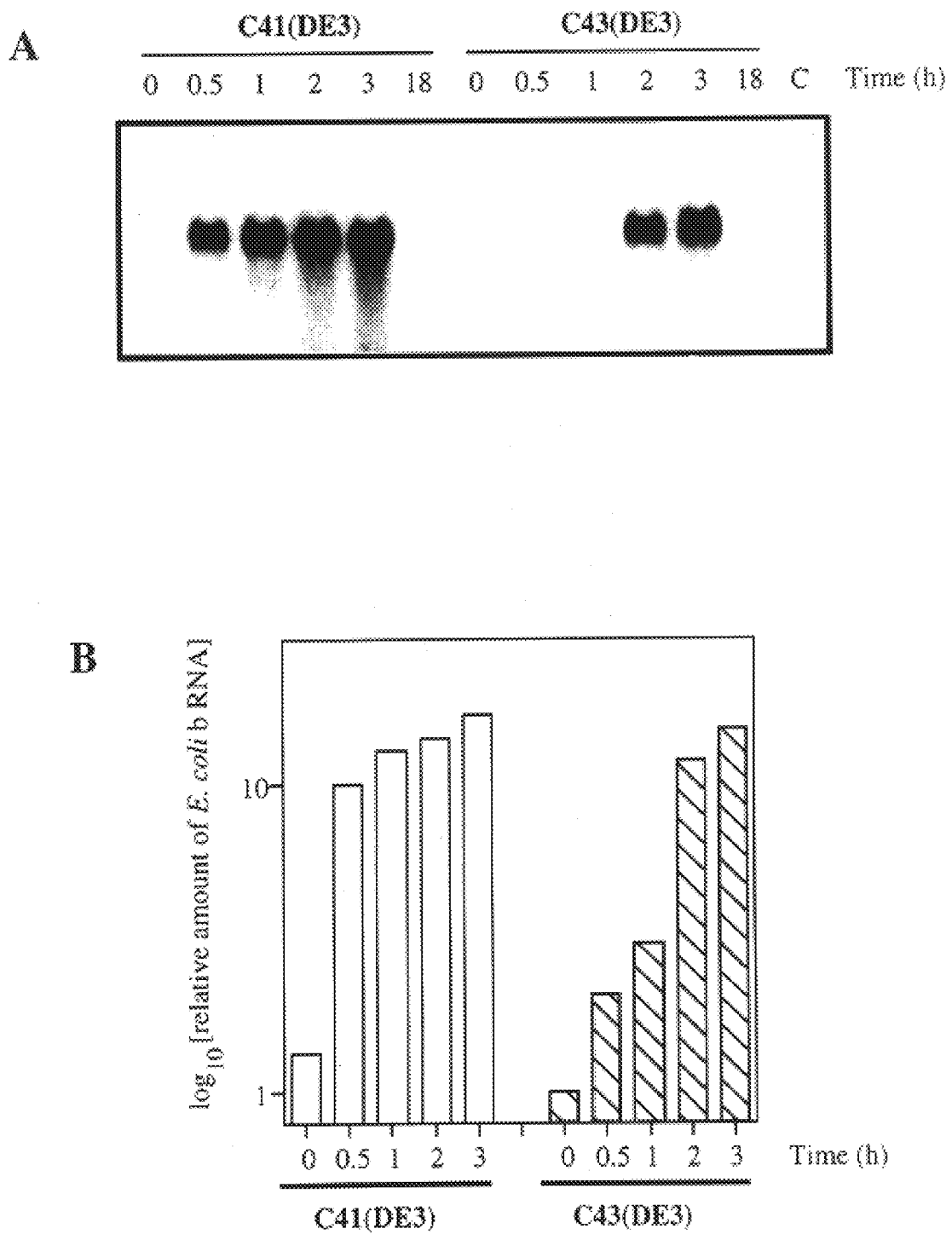
FIG. 5. Analysis of transcripts of *E. coli* F-ATPase b-subunit in C41(DE3) and C43(DE3). Part (A), autoradiography of RNA samples from C41(DE3) and C43(DE3) at various times (shown on top) after induction of expression of F-ATPase subunit b. Lane C contains a control sample of RNA from C41(DE3) cells in which the OGCP had been over-expressed. Part (B), quantitation of the mRNA samples in part (A). In C43(DE3), the signal at time zero is chosen as reference.

A similar comparison of the expression of the b subunit of the *E. coli* F-ATPase in C41(DE3) and C43(DE3) is also conducted (FIG. 5). Experimental details are as for the experiments depicted in FIG. 4. After hybridisation of RNA samples with the probe consisting of the entire coding sequence of the b-subunit, the membrane is exposed to an image plate for 18 hours, and the radioactivity is measured with a Phosphorimager (Molecular Dynamics, Chesham, Bucks HP5 2PX, U.K.). Part (A), autoradiography of RNA samples from C41(DE3) and C43(DE3) at various times (shown on top) after induction of expression of F-ATPase subunit b. Lane C contains a control sample of RNA from C41(DE3) cells in which the OGCP had been over-expressed. Part (B), quantitation of the mRNA samples in part (A). In C43(DE3), the signal at time zero is chosen as reference. The final amount of mRNA for E. coli F-ATPase subunit b accumulated per cell after 3 hours is approximately the same in both strains, but the maximal level of this mRNA is attained in 30 minutes after induction in C41(DE3) and in 2 hours in C43(DE3). The basal level of expression is slightly lower in C43(DE3) than in C41(DE3).

The expression levels of a variety of proteins (seven membrane proteins, ten globular proteins; see Table 1) in BL21(DE3) are compared with the levels achieved in either C41(DE3) or C43(DE3) hosts. For all seven of the membrane proteins, and particularly for the alanine-$H^+$ transporter and the E. coli F-ATPase subunits b and c, expression in the mutant hosts is improved over BL21(DE3). In all three of these latter examples, the induction of the expression both on plates and in liquid media is toxic to C41(DE3) but not to C43(DE3). The gene 10a-alanine-$H^+$ carrier fusion is very well expressed in C43(DE3), and 79 mg of protein are obtained per liter of culture (Table 1). Significant improvements in expression level are also obtained with the ADP/ATP and phosphate carriers in C41(DE3).

A general improvement in the expression of the globular proteins (see Table 1) is also found in mutant host C41 (DE3), including proteins that are well expressed as well as others that are poorly expressed in BL21(DE3). The GFP provides a typical example of the former category. Although it is expressed at 37 mg per liter of culture in BL21(DE3), a four times higher level of expression is obtained in C41(DE3) (see Table 1). The γ-subunit of bovine ATPase provides an example of the second category. Cells of BL21 (DE3) containing pMW7(λ) stopped growing at low density, and the γ-subunit is undetectable by SDS-PAGE analysis of the cells, whereas in C41(DE3) the cells continue to divide, grew to high density and produce a large amount of the γ-subunit (see Table 1).

The RNA polymerase of phage T7 is inhibited by the phage's lysozyme (Moffatt & Studier, 1987), and therefore, co-transformation of a plasmid encoding the lysozyme (pLysS and pLysE) with the plasmid containing the target protein has been advocated as a means of suppressing toxic effects brought about by basal level expression of proteins (Studier et al., 1990). This stratagem has been found to be helpful in some cases of relatively mild toxicity. However, co-transformation of pLysS with pMW7(γ) or with pMW7 (GFP) does not suppress their toxicities on agar plates in the presence of IPTG. In liquid media, the level of expression of both proteins is somewhat higher in BL21(DE3) in the presence of pLys S than in its absence, but the level of expression of both proteins in C41(DE3) is at least twice the level obtained in co-transformed BL21(DE3) cells. Therefore, at least in these two examples C41(DE3) is superior to BL21(DE3)-pLysS as a host for over-expression of proteins.

These studies indicate strongly that a component of toxicity of protein over-expression in E. coli-T7 RNA polymerase systems is linked to transcription of the target gene, and suggest that the toxicity probably arises from the uncoupling of transcription from translation. Where transcription outstrips translation, unstable naked RNA stretches may form (Iost & Dreyfus, 1995; Makarova et al., 1995). By an unknown mechanism, over-expression of either β-galactosidase or an inactive form of elongation factor Tu have been shown to lead to destruction of ribosomal RNAs, and the ensuing lethal effects of over-expression (Dong et al., 1995).

Experiments described above are consistent with this mechanism of lethality of protein over-expression. Strain BL21(DE3) containing the expression plasmid pMW7 (OGCP) produces a large amount of the cognate mRNA from the plasmid, whilst at the same time the target protein is present in the cells at rather low levels. In contrast, in strain C41(DE3) the same transcript is made more slowly, and despite the maximal level being 10 times lower than in BL21(DE3), more of the target protein is synthesised in C41(DE3). Similar effects are noted by comparison of the expression of subunit b of E. coli F-ATPase in C41(DE3) and C43(DE3).

At present, the locations of the mutations in C41(1DE3) and C43(DE3) are not known, but plausible hypotheses concerning the C41(DE3) mutation are that either it affects the activity of the T7 RNA polymerase or that it reduces the amount of polymerase produced. Both effects would probably help to prevent uncoupling of transcription and translation. It is noteworthy that a mutant of T7 RNA polymerase able to transcribe three times more slowly than the wild-type enzyme has been shown to yield about four times more β-galactosidase from an appropriate expression vector (Makarova et al., 1995). The C43(DE3) mutation may also be helping to avoid uncoupling of transcription and translation, but, in addition to delaying the onset of transcription, it also appears to affect the folding and insertion of subunit b into the bacterial membrane. In C41(DE3) the E. coli F-ATPase b subunit accumulates in a form that is difficult to solubilise in the detergent lauryldimethylamine oxide, and it may be mis-folded, whereas in C43(DE3) it is inserted into the membrane and can be readily extracted with the detergent.

A further observation which suggests a mechanism by which the C43(DE3) mutation may operate is that C43(DE3) is Lac$^-$. This suggests a mutation in the Lac operon, possibly extending to the Lac inducing functions (Lac UV5 mutant and wild type repressor) which are coupled to the T7 polymerase gene in the DE3 lysogen. There is a possibility, therefore, that C43(DE3) could comprise a Lac $I^{QS}$ mutant which affects polymerase induction.

Membrane Protein Expression

To date, the usage of strain C43(DE3) for expression of other toxic proteins has been explored in a number of examples including the F-ATPase b- and c-subunits and the alanine-$H^+$ carrier. See Table 1. A number of examples show that if the protein is already expressed without toxic effect in C41(DE3), then no additional benefit derives from overexpression of the same protein in C43(DE3). However, membrane proteins especially which retain a degree of toxicity in C41(DE3) are better expressed in C43(DE3).

Genes encoding bovine MPCP, bovine ADP/ATP translocase, Bacillus PS3 alanine/$H^+$ carrier, as well as E. coli F-ATPase subunits b and c are inserted in C41(DE3) and C43(DE3) cells on pMW vectors. After growth as described in the preceding examples, cells are harvested and the proteins isolated. All of the above proteins are expressed more effectively in C43(DE3) than in C41(DE3), as shown in Table 1.

Periplasmic Localisation

A nucleic acid sequence encoding the globular E. coli protein Tol is fused to a periplasmic localisation sequence and inserted into a pET vector under the control of the T7 promoter and transfected into C41(DE3) and C43(DE3) cells. When expressed according to the foregoing protocols, translocation to the periplasm is observed to be of the order of 10% in C41(DE3) hosts, but 70 to 80% in C43(DE3) hosts.

Example 4

Solubility of Expressed Proteins

It is observed that, in general, proteins which are insoluble in BL21(DE3) hosts remain insoluble in hosts according to the invention. However, the solubility of proteins which are partially soluble in BL21(DE3) may be enhanced, especially when cultured at a the reduced temperature of 25° C.

Human poly(ADP-ribose) polymerase, amino acids 1 to 330 (DNA binding site) is inserted into pMW7 and transfected into BL21(DE3) and C41(DE3) hosts. After culture as described in Example 2 and induction for 3 hours at 37° C., the cells are disrupted and the localisation of the protein product determined. For comparable levels of protein expression, in BL21(DE3) cells, 10 to 20% of the product is located in the cytoplasm, with the remaining product being precipitated in the form of inclusion bodies. In C41(DE3), however, the product is 90% soluble.

The results obtained are protein-dependent; some proteins are more soluble than others. Moreover, many proteins which remain insoluble even in C41(DE3) when cultured at 37° C. are soluble when cultured at 25° C.

Further increases in solubility may be obtained using C43(DE3) cells. A globular protein expressed from a pET vector in C41(DE3) and C43(DE3) cells at 25° C. shows 50% solubility in C41(DE3). In C43(DE3) cells the solubility is 100%, but the yield is slightly reduced.

Example 5

Targeting of Proteins to the Membrane

As described in Example 3, membrane proteins are effectively produced in C43(DE3) and incorporated into the membrane. C43(DE3) is capable of increased synthesis of cellular membranes in which membrane proteins may be incorporated.

In order to increase the incorporation potential of membrane proteins which do not, in themselves, increase membrane synthesis in C43(DE3), a two vector system is developed which provides for induction of membrane synthesis before induction of the desired membrane protein, thus providing for membrane incorporation of high amounts of desired membrane protein.

The first vector is the pMW7 vector encoding E. coli lactose permease. The second vector is a pBAD 30 vector (Guzman et al., 1995) comprising a $P_{BAD}$ promoter from the E. coli arabinose operon and a pACYC origin of replication. A coding sequence encoding the b subunit of E. coli F-ATPase is inserted into the MCS of pBAD 28.

Both vectors are cotransfected into C43(DE3) cells and the cells grown under IPTG induction in order to induce expression of the F-ATPase b subunit gene. After culture for 18 hours at 25° C., the cells are spun down and transferred to fresh medium, supplemented with arabinose in order to induce expression of the $P_{BAD}$ promoter driving the lactose permease gene.

Cells are cultured for a further 18 hours, disrupted using a french press and the membrane fraction spun down. Lactose permease can be isolated in large amounts from the membranes. In contrast, the cytosolic fraction is virtually free of lactose permease.

Membrane Protein Fusion

In a variation of the above method, non-membrane proteins or membrane proteins which insert poorly into the membrane may be fused with the b subunit of E. coli F-ATPase in order to target them to the membrane. In the case of targeted membrane proteins, the proteins themselves are inserted into the membrane.

A fusion of OGCP (a poorly targeting membrane protein recovered in inclusion bodies) and F-ATPase b subunit is constructed and inserted into the pBAD 28 vector as described in the preceding example. Upon expression in C43(DE3) in which membrane synthesis has been previously induced by expression of F-ATPase b subunit alone, the OGCP fusion is targeted to the membrane fraction and may be recovered therefrom as described above.

Example 6

Screening

The neurotensin receptor (NTR) has been shown to be functional in E. coli when fused to the periplasmic maltose binding protein, MalE (Bertin et al., 1992; Tucker and Grisshammer, 1996). As described in example 5, two expression vectors are transformed into the E. coli C43 (DE3) host strain. They are the pBAD(Ecb) vector encoding the b subunit of the F-ATPase under the control of the arabinose promoter, and pMW7(MalE-NTR) encoding the fusion protein between MalE and the neurotensin receptor. Freshly transformed E. coli C43(DE3) host cells are grown for 18 hours at 37° C. in rich media containing arabinose in order to induce a low level of expression of the b subunit. The amount of arabinose in the medium is adjusted to obtain the minimal level of the b subunit for the maximal amount of proliferated membrane. Then IPTG is added to the medium and incubation is continued for a further 24 hours. The MalE-NTR fusion protein accumulates preferentially in the proliferated internal membranes rather than in the cytoplasmic membranes. Cells are harvested by centrifugation and passed twice through a pre-cooled French press cell. The internal membranes are isolated by differential centrifugation and purified by sucrose density gradient centrifugation. Ten to twenty milligrams of the fusion protein MalE-NTR are recovered per liter of culture. The MalE-NTR fusion protein is found almost exclusively in the proliferated membranes. Since the level of contamination by other membrane proteins is very low, these "in vivo formed liposomes" can be used directly for high throughput ligand screening, and there is no necessity to purify the MalE-NTR fusion protein further and to reconstitute it into membranes. Phospholipid levels in the membranes thus obtained is determined and the phospholipid composition of the membranes is adjusted closer to those of the membranes where the NTR is naturally found.

The liposomes containing the MalE-NTR fusion protein are bound to a support compatible with the Biocore system. A library of ligands is generated and ligands are screened for their ability to bind the fusion protein. Ligands having a high binding constant to the MalE-NTR fusion protein are analysed further in vitro in the presence of GTP-coupled proteins.

Deposition Data

The following microorganisms have been deposited at the stated depositary institutions in accordance with the Budapest Treaty:

E. coli C43(DE3) was deposited at the European Collection of Cell Cultures (ECCC), Salisbury, Wiltshire, UK on Jul. 4, 1996 under accession number B96070445;

E. coli C41(DE3) deposited at the ECCC on Jul. 4, 1996 under accession number B96070444;

E. coli C0214(DE3) deposited at the National Collections of Industrial and Marine Bacteria Limited (NCIMB; 23 St. Machar Drive, Aberdeen AB2 1RY, Scotland, UK) on Jun. 25, 1997 under accession number NCIMB 40884;

E. coli DK8(DE3)S deposited at the National Collections of Industrial and Marine Bacteria Limited (NCIMB; 23 St. Machar Drive, Aberdeen AB2 1RY, Scotland, UK) on Jun. 25, 1997 under accession number NCIMB 40885.

TABLE 1

| Protein[1] | Location[2] | BL21 | C41 | C43 |
|---|---|---|---|---|
| Bovine OGCP (m) | IB | 10a | 100a | 84a |
| Bovine phosphate carrier (m) | IB | 5a | 35a | 52a |
| Bovine ADP/ATP translocase (m) | IB | — | 9a | 18a |
| Bacillus PS3 alanine/H+ carrier (m) | IB | — | 19b | 79b |
| E. coli F-ATPase subunit b (m) | IB/M | — | 8b | 25b |
| E. coli F-ATPase subunit c (m) | M | 2b | 10b | 15b |
| Bovine F-ATPase subunit bc (m) | IB | ND | 30b | ND |
| Bovine F-ATPase subunit α (g) | IB | 35b | 135b | ND |
| Bovine F-ATPase subunit β (g) | IB | 50b | 240b | ND |
| Bovine F-ATPase subunit γ (g) | IB | 11b | 74b | ND |
| Bovine F-ATPase subunit δ (g) | IB | 4b | 18b | ND |
| Bovine F-ATPase subunit d (g) | IB | 10b | 20b | 3b |
| Bovine F-ATPase subunit OSCP (g) | IB | 50a | 300a | ND |
| Bovine F-ATPase subunit F6 (g) | C | 65b | 130b | ND |
| Bovine F-ATPase inhibitor protein (g) | C | 8b | 70b | ND |
| D melanogaster staufen protein (g) | C | — | ND | ND |
| Aequoria victoria GFP (g) | IB/C | 37b | 140b | ND |

Legend for Table 1:

[1] m, membrane protein, g, globular protein; [2] IB, inclusion bodies; C, soluble in cytosol; M, in membrane; for E. coli F-ATPase subunit b, IB/M indicates that in C41(DE3), the protein is in a form that is difficult to solubilise in detergent, but in C43(DE3) it is in the membrane and is readily detergent extractable (see text); for the GFP, IB/C indicates that the protein is partially soluble and partially in inclusion bodies in both BL21(DE3) and C41(DE3). [3] The expression level is given as mg protein/liter of bacterial cells, quantified by, [a] bicinchoninic acid assay, or [b] N-terminal sequencing. A portion of cells is solubilised in 1% SDS, and the proteins are separated by SDS-PAGE (Laemmli, 1970), transferred to polyvinylidene difluoride membranes and stained with PAGE 83 dye. Appropriate bands are excised and introduced into the sequencer. The yields of phenylthiohydantoins released at each of 15 consecutive cycles of Edman degradation are measured by HPLC, and the amount of the protein of interest on the membrane is estimated by extrapolation to cycle zero. Each experiment is performed twice. [c] The bovine F-ATPase b-subunit probably has two trans-membrane spanning α-helices and is not related in sequence to the E. coli b-subunit, which has one trans-membrane span (Walker et al., 1987); [d], the staufen protein is detected in the soluble fraction of the cells by Western blotting by D. St. Johnston. A hyphen indicates that because of toxicity of the expression plasmid, no expression is obtained. ND, not determined. With the exceptions of the alanine-H+ carrier, which is cloned in pCGT180 (kindly donated by Dr. C. G. Tate, it is derived from pGEMX and producing a fusion protein with the major capsid protein 10A of phage T7), and the staufen protein which is cloned into pET7, the coding sequences of the various proteins are cloned into pMW7 (Way et al., 1990). Also, see Collinson et al. (1994) and Orriss et al. (1996) for more details of vectors, and Chalfie et al. (1994) for details of the GFP.

REFERENCES

Ausubel, F. M., Brent, R., Kingston, R. E., Seidman, D. D., Smith, J. G., Struhl, J. A. & Struhl, K. (1987). *In Current Protocols in Molecular Biology.* John Wiley & Sons Inc., New York.

Bertin, B., Freissmuth, M., Breyer, R. M., Schutz, W., Stosberg, A. D., and Marullo, S. (1991). Functional expression of the human serotonin 5-HT1A receptor in *Escherichia coli. J. Biol. Chem.,* 267, 8200–8206.

Chalfie, M., Tu, Y., Euskirchen, G., Ward, W. W. & Prasher, D. C. (1994). Green fluorescent protein as a marker for gene expression. *Science* 263, 802–805.

Chapot, M. P., Eshdat, Y., Marullo, S., Guillet, J. G., Charbit, A., Strosberg, A. D., Delavier-Klutchko, C. (1990). Localization and characterization of three different beta-adrenergic receptors expressed in *Escherichia coli. Eur J Biochem* 187 (1): 137–144.

Collinson, I. R., van Raaij, M. J., Runswick, M. J., Fearnley, I. M., Skehel, J. M., Orriss, G., Miroux, B. & Walker, J. E. (1994). ATP synthase from bovine heart mitochondria: in vitro assembly of a stalk complex in the presence of $F_1$-ATPase and in its absence. *J. Mol. Biol.* 242, 408–421.

de Boer et al., (1983) PNAS (USA) 80:21–25.

de Boer, P. A. J., Crossley, R. E. & Rothfield, L. I. (1988). Isolation and properties of min B, a complex genetic locus involved in correct placement of the division site in *Escherichia coli. J. Bact.* 170, 2106–2112.

Doherty, A. J., Connolly, B. A. & Worrall, A. F. (1993). Overproduction of the toxic protein bovine pancreatic DNAse I in *Escherichia coli* using a tightly controlled T7 promoter based vector. *Gene* 136, 337–340.

Dong, H., Nilsson, L. & Kurland, C. G. (1995). Gratuitous overexpression of genes in *Escherichia coli* leads to growth inhibition and ribosome destruction. *J. Bacteriol.* 177, 1497–1504.

Fiermonte, G., Walker, J. E. & Palmieri, F. (1993). Abundant bacterial expression and reconstitution of an intrinsic membrane transport protein from bovine mitochondria. *Biochem. J.* 294, 293–299.

Fillingame, R. H. (1990). Molecular mechanics of ATP synthesis by $F_1F_O$-type $H^+$-transporting ATPases. *The Bacteria* 12, 345–391.

Friedberg, E. C., Walker, G. C. & Siede, W. (1995). In *DNA repair and mutagenesis.* ASM Press, Washington D.C.

George, J. W., Brosh Jr, R. M. & Matson, S. W. (1994). A dominant negative allele of the *Escherichia coli* uvrD gene encoding DNA helicase II. *J. Mol. Biol.* 235, 424–435.

Grisshammer, R. & Tate, C. G. (1995). Overexpression of integral membrane proteins for structural studies. *Qu. Rev. Biophys.* 28, 315–422.

Guzman et al., (1995) J. Bacteriol. 177:4121–4130.

Guzman, L. M., Barondess, J. J. & Beckwith, J. (1992). Fts L, an essential cytoplasmic membrane protein involved in cell division in *Escherichia coli. J. Bacteriol.* 174, 7716–7728.

Hockney, R. C. (1994). Recent developments in heterologous protein production in *Escherichia coli. Trends Biotechnol.* 12, 456–463.

Iost, I. & Dreyfus, M. (1995). The stability of *Escherichia coli* lacZ mRNA depends upon the simultaneity of its synthesis and translation. *EMBO J.* 14, 3252–3261.

Kamata, H., Akiyama, S., Morosawa, H., Ohta, T., Hamamoto, T., Kambe, T., Kagawa, Y. & Hirata, H. (1992). Primary structure of the alanine carrier protein of thermophilic bacterium PS3. *J. Biol. Chem.* 267, 21650–21655.

Kane, J. F. (1995). Effects of rare codon clusters on high-level expression of heterologous proteins in *Escherichia coli. Curr. Opinion Biotechnol.* 6, 494–500.

Kiefer, H., J. Krieger, J. D. Olszewski, G. Von Heijne, G. D. Prestwich, and H. Breer. (1996). Expression of an olfactory receptor in *Escherichia coli:* purification, reconstitution, and ligand binding. *Biochemistry* 35:16077–16084.

Laemmli, U. K. (1970). Cleavage of structural proteins during the assembly of the head of bacteriophage T4. *Nature* 227, 680–685.

Makarova, O. V., Makarov, E. M., Sousa, R. & Dreyfus, M. (1995). Transcribing of *Escherichia coli* genes with mutant T7 RNA polymerases: Stability of lacZ mRNA inversely correlates with polymerase speed. *Proc. Natl. Acad. Sci. U.S.A.* 92, 12250–12254.

Moffatt, B. A. & Studier, F. W. (1987). T7 lysozyme inhibits transcription by T7 RNA polymerase. *Cell* 49, 221–227.

Murli, S. & Walker, G. C. (1993). SOS mutagenesis. *Current Opinion Genetics and Development* 3, 719–725.

Orriss, G. L., Runswick, M. J., Collinson, I. R., Miroux, B., Fearnley, I. M., Skehel, J. M. & Walker, J. E. (1996). The δ- and ε-subunits of bovine $F_1$-ATPase interact to form a heterodimeric subcomplex. *Biochem. J.* 314, 695–700.

Runswick, M. J., Powell, S. J., Nyren, P. & Walker, J. E. (1987). Sequence of the bovine mitochondrial phosphate carrier protein: structural relationship to ADP/ATP translocase and the brown fat mitochondrial uncoupling protein. *EMBO J.* 6, 1367–1373.

St. Johnston, D., Beuchle, D. & Nüsslein-Volhard, C. (1991). Staufen, a gene required to localise maternal RNAs in the Drosophila egg. *Cell* 66, 51–63.

Studier. F. W., Rosenberg, A. H., Dunn, J. J. & Dubendorff, J. W. (1990). Use of T7 RNA polymerase to direct expression of cloned genes. *Methods in Enzymol.* 185, 60–89.

Tucker, J., and Grisshammer R. (1996). Purification of a rat neurotensin receptor expressed in *Escherichia coli*. *Biochem. J.* 317, 891–899.

Uzan, M., Favre, R. & Brody, E. (1988). A nuclease that cuts specifically in the ribosome binding site some T4 mRNAs. *Proc. Natl. Acad. Sci. U.S.A.* 85, 8895–8899.

Walker. J. E. & Runswick, M. J. (1993). The mitochondrial transport protein super-family. *J. Bioenerget. Biomembranes* 25, 435–467.

Walker, J. E., Runswick, M. J. & Poulter, L. (1987). ATP synthase from bovine mitochondria: characterisation and sequence analysis of two membrane associated subunits and of their corresponding c-DNAs. *J. Mol. Biol.* 197, 89–100.

Way, M., Pope, B., Hawkins, M. & Weeds, A. G. (1990). Identification of a region in segment 1 of gelsolin critical for actin binding. *EMBO J.* 9, 4103–4109.

What is claimed is:

1. A method for selecting an *E. coli* cell mutant which is resistant to expression system toxicity, comprising the steps of growing an *E. coli* cell transformed with an expression vector, inducing the expression vector such that a toxic effect on said cell is observed, and recovering a viable *E. coli* cell in which the expression vector continues to function, wherein said *E. coli* cell mutant does not comprise a mutation in said expression vector, and wherein the cell recovered is an *E. coli* cell mutant which is resistant to expression system toxicity.

2. A method according to claim 1 wherein the resistance of the host cell mutant to expression system toxicity is not specific to a target protein expressed in the expression system.

3. A method according to claim 1 or claim 2 wherein the mutant host cell exhibits a general or specific decrease in metabolic activity over a non-mutant host cell.

4. The method of claim 1, wherein the expression vector comprises a selectable marker.

5. A method for improving an expression system comprising the steps of:
   (a) providing an *E. coli* host cell transformed with an inducible expression vector encoding a target polypeptide and a selectable marker;
   (b) culturing the cell transformed with the expression vector under selection pressure compatible with the selectable marker;
   (c) inducing the expression system to produce the target polypeptide, such that a toxic effect is observable in said cell;
   (d) recovering cells from the culture and growing them under a selection pressure and inducing conditions; and
   (e) recovering a viable *E. coli* cell which continues to produce the target polypeptide.

6. The method of claim 5 wherein the target polypeptide is a foreign or endogenous membrane protein.

7. The method of claim 5 wherein the transformed host cell expresses a bacteriophage RNA polymerase and wherein the expression system comprises a promoter sequence recognized by the polymerase.

8. The method of claim 7 wherein the polymerase is T7 RNA polymerase.

9. The method of claim 7 wherein the expression system comprises the expression vector pET or pMW7.

10. The method of claim 5 wherein the expression vector comprises a nucleic acid sequence encoding a polypeptide which serves as a detectable label.

11. The method of claim 10 wherein the detectable label is Green Fluorescent Protein.

12. A method for the preparation of a recombinant polypeptide which method comprises:
   (a) transforming a host cell, produced by the application of two rounds of selection via the method of claim 1 or claim 5, with a vector comprising a gene encoding the polypeptide;
   (b) culturing the transformed host cell under conditions which allow expression of the polypeptide; and
   (c) recovering the polypeptide.

13. The method of claim 12 wherein the host cells are cultured at 25° C.

14. The method according to claim 12 wherein the host cell is selected from the group consisting of *E. coli* C43 (DE3) (ECCC B96070445) and *E. coli* C2014(DE3) (NCIMB 40884).

15. A method for the preparation of a membrane protein which method comprises:
   (a) transforming a host cell, produced by the application of two rounds of selection via the method of claim 1 or claim 5, with a vector comprising a gene encoding the membrane protein;
   (b) culturing the transformed host cell under conditions which allow expression of the membrane protein; and
   (c) disrupting the cells and recovering the membrane protein from the membrane fraction thereof.

16. The method according to claim 15 wherein the host cell is selected from the group consisting of *E. coli* C43 (DE3) (ECCC B96070445) and *E. coli* C2014(DE3) (NCIMB 40884).

17. A method for producing a membrane protein, comprising the steps of:
   (a) transforming an *E. coli* cell, produced by the application of two rounds of selection via the method of claim 1 or claim 5, with a first expression unit and a second expression unit, wherein the first expression unit expresses the β subunit of *E. coli* F-ATPase under the control of a first inducible promoter and the second expression unit expresses the desired membrane protein under the control of a second inducible promoter;
   (b) inducing expression of *E. coli* F-ATPase β subunit from the first expression unit, and culturing the resulting cell such that membrane production is induced;

(c) inducing expression of the desired membrane protein from the second expression unit and culturing the resulting cell to produce the desired membrane protein; and (d) disrupting the cell of step (c), separating the membrane and cytosolic fractions and recovering the desired membrane protein from the membrane fraction.

18. The method of claim 17 wherein the *E. coli* cell is selected from the group consisting of *E. coli* C43(DE3) (ECCC B96070445), *E. coli* C41(DE3) (ECCC B96070444), *E. coli* DK8(DE3)S (NCIMB 40885) and *E. coli* C2014(DE3) (NCIMB 40884).

19. A method for directing an expressed polypeptide to the periplasmic space of a bacterial host cell, comprising expressing the polypeptide fused to a periplasmic localization sequence in a host cell produced by the application of two rounds of selection via the method of claim 1 or claim 5.

20. The method according to claim 19 wherein the host cell is selected from the group consisting of *E. coli* C43 (DE3) (ECCC B96070445) and *E. coli* C2014(DE3) (NCIMB 40884).

21. An *E. coli* cell selected from the group consisting of *E. coli* C41(DE3) (ECCC B96070444) and *E. coli* DK8 (DE3)S (NCIMB 40885).

22. An *E. coli* cell selected from the group consisting of *E. coli* C43(DE3) (ECCC B96070445) and *E. coli* C2014 (DE3) (NCIMB 40884).

* * * * *